United States Patent
Beller et al.

(10) Patent No.: US 9,993,463 B2
(45) Date of Patent: *Jun. 12, 2018

(54) USE OF MALEIMIDE DERIVATIVES FOR PREVENTING AND TREATING CANCER

(71) Applicant: CENTOGENE AG, Rostock (DE)

(72) Inventors: Matthias Beller, Nienhagen (DE); Jan Lukas, Rostock (DE); Moritz Frech, Neu Broderstorf (DE); Christian Junghanss, Rostock (DE); Arndt Rolfs, Berlin (DE); Anahit Pews-Davtyan, Rostock (DE)

(73) Assignee: Centogene AG, Rostock (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/651,053

(22) PCT Filed: Dec. 10, 2013

(86) PCT No.: PCT/EP2013/003730
§ 371 (c)(1),
(2) Date: Jun. 10, 2015

(87) PCT Pub. No.: WO2014/090396
PCT Pub. Date: Jun. 19, 2014

(65) Prior Publication Data
US 2015/0313882 A1 Nov. 5, 2015

(30) Foreign Application Priority Data
Dec. 10, 2012 (EP) .................................. 12008231

(51) Int. Cl.
| | |
|---|---|
| A61K 31/40 | (2006.01) |
| A61K 31/437 | (2006.01) |
| C07D 401/14 | (2006.01) |
| A61K 31/404 | (2006.01) |
| C07D 403/04 | (2006.01) |
| C07D 403/14 | (2006.01) |
| C07D 405/04 | (2006.01) |
| C07D 409/14 | (2006.01) |
| C07D 471/04 | (2006.01) |
| C07D 487/04 | (2006.01) |
| A61K 45/06 | (2006.01) |

(52) U.S. Cl.
CPC .......... *A61K 31/437* (2013.01); *A61K 31/404* (2013.01); *A61K 45/06* (2013.01); *C07D 401/14* (2013.01); *C07D 403/04* (2013.01); *C07D 403/14* (2013.01); *C07D 405/04* (2013.01); *C07D 409/14* (2013.01); *C07D 471/04* (2013.01); *C07D 487/04* (2013.01)

(58) Field of Classification Search
CPC .... A61K 31/437; A61K 45/06; A61K 31/404; A61K 2300/00; C07D 401/14; C07D 403/04; C07D 403/14; C07D 405/04; C07D 409/14; C07D 471/04; C07D 487/04
See application file for complete search history.

(56) References Cited

U.S. PATENT DOCUMENTS 7,405,305 B2 * 7/2008 Albaugh .............. C07D 401/14
546/184

FOREIGN PATENT DOCUMENTS

| JP | H03-094686 | 4/1991 | |
|---|---|---|---|
| WO | WO 99/42100 | 8/1999 | |
| WO | WO 02/038561 A1 | 5/2002 | |
| WO | WO 03/095452 A1 | 11/2003 | |
| WO | WO 03/103663 A2 | 12/2003 | |
| WO | 2006/061212 A1 | 6/2006 | |
| WO | WO 2007/008514 A2 | 1/2007 | |
| WO | 2009/071620 A1 | 6/2009 | |
| WO | WO 2009071620 A1 * | 6/2009 | ........... A61K 31/404 |
| WO | WO 2011/073091 A1 | 6/2011 | |
| WO | WO 2011/073092 A1 | 6/2011 | |

(Continued)

OTHER PUBLICATIONS

Katoh et al ( Bioorganic & Medicinal Chemistry Letters, 2005, 15, 3109-3113).*
Kadri et al (Industrial Crops and Products, 2014, 54, 6-12).*
International Search Report dated Jul. 1, 2014 from PCT International Application No. PCT/EP2013/003730.
Pews-Davtyan, Anahit, et al., "Efficient palladium-catalyzed synthesis of 3-aryl-4-indolylmaleimides," Organic & Biomolecular Chemistry, vol. 6, No. 6, Jan. 1, 2008, p. 992.
Heidel, Florian H., et al., "3,4-Diarylmaleimides—a novel class of kinase inhibitors—effectively induce apoptosis in FLT3-ITD-dependent cells," Annals of Hematology Mar. 2012, vol. 91, No. 3, Mar. 2012, pp. 331-344.
Ganser, Christopher, et al., "Novel 3-Azaindolyl-4-arylmaleimides exhibiting potent antiangiogenic efficacy, protein kinase inhibition, and antiproliferative activity," Journal of Medicinal Chemistry Nov. 26, 2012, vol. 55, No. 22, Nov. 26, 2012, pp. 9531-9540.
Hilliard, Tyvette S., et al. "Glycogen synthase kinase 3[beta] inhibitors induce apoptosis in ovarian cancer cells and inhibit in-vivo tumor growth," Anti-Cancer Drugs Nov. 2011, vol. 22, No. 10, Nov. 2011, pp. 978-985.

(Continued)

*Primary Examiner* — Rachael Bredefeld
*Assistant Examiner* — Ibrahim D Bori
(74) *Attorney, Agent, or Firm* — Ward and Smith, P.A.

(57) ABSTRACT

The present invention is related to a compound of formula (I) a pharmaceutically acceptable salt thereof, a hydrate thereof, a solvate thereof, a metabolite thereof or a prodrug thereof; for use in a method for the treatment and/or prevention of cancer, wherein X is selected from the group consisting of N—$R^1$, O and S; R1 is selected from the group consisting of alkyl, cycloalkyl, aryl, arylalkyl and hydrogen; $R^2$ is selected from the group consisting of indolyl, substituted indolyl, azaindolyl and substituted azaindolyl; and $R^3$ is selected from the group consisting of aryl, substituted aryl, unsubstituted heteroaryl, heterocyclyl and substituted heterocyclyl.

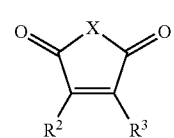

(I)

6 Claims, 5 Drawing Sheets

(56) References Cited

FOREIGN PATENT DOCUMENTS

WO    WO 2014/090398 A1    6/2014

OTHER PUBLICATIONS

Peifer, C., et al., "Design, synthesis, and biological evaluation of novel 3-aryl-4-(1H-indolo-3yl)-1,5-dihydro-2H-pyrrole-2-ones as vascular endothelial growth factor receptor (VEGF-R) inhibitors," Journal of Medicinal Chemistry, American Chemical Society, US, vol. 51, Jan. 1, 2008, pp. 3814-3824.
Eisenloffel, Christian, et al., "Interference of a novel indolylmaleimide with microtubules induces mitotic arrest and apoptosis in human progenitor and cancer cells," Biochemical Pharmacology, vol. 85, No. 6, Mar. 1, 2013, pp. 763-771.
Notification of Reasons for Rejection, Japanese Patent Application No. 2015-545699, Sep. 5, 2017, 30 pages.
Schmole et al., "Novel indolylmaleimide acts as GSK-3β inhibitor in human neural progenitor cells," Bioorganic & Medicinal Chemistry, 2010, 18, pp. 6785-6795.
Shorunov et al., "A Convenient Synthesis of 3,4-Diaryl(hetaryl)-Substituted Maleimides and Maelic Anhydrides," Russian Journal of Organic Chemistry, 2006, vol. 42, No. 10, pp. 1490-1497.
Song et al., "Glycogen synthase kinase-3β inhibitors suppress leukemia cell growth," Experimental Hematology, 2010, 38, pp. 908-921.
Xu et al., "Synthesis and Cytotoxicity of Indolopyrrolemaleimides," Chem. Pharm. Bull., 2007, 55(9), pp. 1302-1307.

* cited by examiner

USE OF MALEIMIDE DERIVATIVES FOR PREVENTING AND TREATING CANCER

CROSS-REFERENCE TO RELATED APPLICATIONS

This application is a 35 U.S.C. § 371 National Stage Entry of International Application No. PCT/EP2013/003730 having an international filing date of Dec. 10, 2013, which claims the benefit of European Application No. EP 12 008 231.8 filed Dec. 10, 2012, the contents of which are herein incorporated by reference in their entirety.

The present invention relates to a chemical compound of formula (I), its use in the treatment of a disease, a pharmaceutical composition comprising the compound, and a method for the treatment of a disease.

Cancer is the second leading cause of death in many countries, exceeded only by heart disease. Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer therapy is a rapidly evolving field of science, nowadays growing more and more into targeted therapies, employing antibodies to cancer specific epitopes or small molecules interfering with cancer-specific pathways. Even in the face of these great progressions there is still a high clinical value and a strong need for innovations, due to better understood resistances, high toxicities and adverse effects for drugs affecting the microtubules in eukaryotic cells. Such microtubule-binding agents can be classified by their affinity to different binding sites on microtubules and/or αβ-tubulin heterodimers. These drugs impair the balance of 'dynamic instability' in microtubules by either promoting their assembly and stability or by impairing the assembly of tubulin heterodimers, thus particularly interfering with cell progression during mitosis, ultimately supporting induction of apoptosis (Matson and Stukenberg, Spindle poisons and cell fate: a tale of two pathways. Mol. Interv. 11, 2011). Indoles from natural sources, as well as semi-synthetic and synthetic products have been described to display anti-mitotic features due to inhibition of tubulin polymerization, most of them by binding to the colchicine site (Brancale and Silvestri, Indole, a core nucleus for potent inhibitors of tubulin polymerization. Med. Res. Rev. 27, 2007). Especially the tubulin-inhibiting agents have given rise to a set of small molecules, among them the combrestatins as lead substances, interfering with cancer vasculature, a promising target in anticancer therapy (Kanthou and Tozer, Microtubule depolymerizing vascular disrupting agents: novel therapeutic agents for oncology and other pathologies. Int. J. Exp. Pathol. 90, 2009). Thus small molecules containing an indole as core structure are of special interest to be employed in cancer treatment.

The problem underlying the present invention is the provision of a means suitable for the treatment of cancer. A further problem underlying the present invention is the provision of a pharmaceutical composition suitable for the treatment of cancer. A still further problem underlying the present invention is the provision of a method for the treatment of cancer.

The problem underlying the present invention is solved by the subject matter of the attached independent claims, preferred embodiments may be taken from the attached dependent claims. Further aspects of the invention and various embodiments thereof are disclosed in the following.

Embodiment 1

A compound of formula (I):

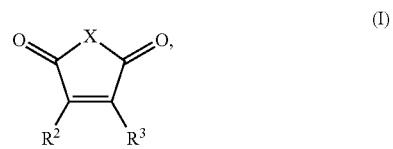

a pharmaceutically acceptable salt thereof, a hydrate thereof, a solvate thereof, a metabolite thereof or a prodrug thereof; for use in a method for the treatment and/or prevention of cancer,
wherein
X is selected from the group consisting of N—$R^1$, O and S;
$R^1$ is selected from the group consisting of alkyl, cycloalkyl, aryl, arylalkyl and hydrogen;
$R^2$ is selected from the group consisting of indolyl, substituted indolyl, azaindolyl and substituted azaindolyl; and
$R^3$ is selected from the group consisting of aryl, substituted aryl, unsubstituted heteroaryl, heterocyclyl and substituted heterocyclyl.

Embodiment 2

The compound of embodiment 1, wherein
$R^2$ comprises one, two, three, four, five or six substituents, whereby each and any of the substituents is individually and independently selected from the group comprising halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 3

The compound of any one of embodiments 1 to 2, wherein $R^3$ comprises one, two, three, four, five, six or seven substituents, whereby each and any of the substituents is individually and independently selected from the group comprising hydrogen, alkyl, alkenyl, alkynyl, aryl, acyl, formyl, halogen, haloalkyl, alkylthio, monoalkylamino, dialkylamino, monoarylamino, diarylamino, alkylarylamino, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 4

The compound of any one of embodiments 1 to 3, wherein
X is N—$R^1$, and wherein
$R^1$ is preferably selected from the group consisting of alkyl, hydrogen, phenyl and benzyl.

Embodiment 5

The compound of embodiment 4, wherein
$R^1$ is selected from the group consisting of methyl, butyl and hydrogen, preferably $R^1$ is selected from the group consisting of methyl and hydrogen.

Embodiment 6

The compound of any one of embodiments 1 to 3, wherein X is O.

Embodiment 7

The compound of any one of embodiments 1 to 6, preferably any one of embodiments 4 to 6, wherein
$R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 8

The compound of embodiment 7, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted indolyl, substituted thiophenyl and substituted pyridinyl.

Embodiment 9

The compound of embodiment 8, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 10

The compound of embodiment 9, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 11

The compound of embodiment 8, wherein $R^3$ is substituted phenyl and each and any of the substituents is individually any independently selected from the group consisting of alkyl, substituted alkyl, alkoxy, substituted alkoxy, alkynly and halogen.

Embodiment 12

The compound of embodiment 11, wherein
alkyl is methyl or ethyl,
substituted alkyl is halogen-substituted methyl or acetyl,
alkoxy is ethoxy, and
alkynyl is vinyl.

Embodiment 13

The compound of embodiment 8, wherein the compound is of formula (IV)

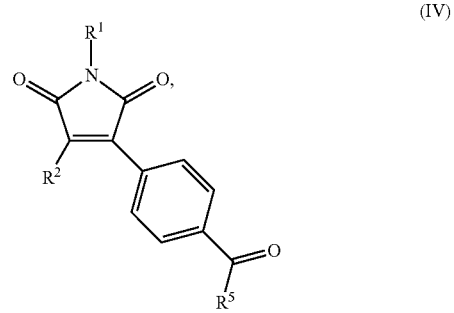

wherein $R^5$ is selected from the group consisting of alkyl, aminoalkyl, alkoxyalkyl, hydroxyalkyl, aryl and heteroaryl.

Embodiment 14

The compound of embodiment 13, wherein
$R^5$ is methyl.

Embodiment 15

The compound of any of embodiments 1 to 14, preferably any one of embodiments 1 to 6, more preferably any one of embodiments 4 to 6, wherein each and any of indolyl, substituted indolyl, azaindolyl and substituted azaindolyl of $R^2$ is individually and independently either unprotected or protected at N, preferably at N of the 5-membered ring.

Embodiment 16

The compound of any one of embodiments 1 to 15, preferably any one of embodiments 1 to 6, more preferably any one of embodiments 4 to 6, wherein
$R^2$ is a moiety of formula (VIa)

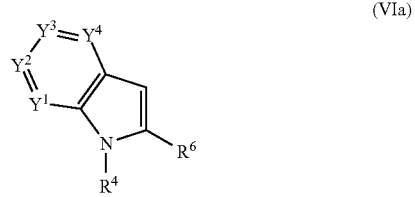

wherein
$R^4$ is selected from the group consisting of hydrogen, aryl, heteroaryl, alkyl, cycloalkyl, polyfluoroalkyl, arylalkyl and heteroarylalkyl, $R^6$ is selected from the group consisting of alkyl and aryl, each and any of $Y^1$, $Y^2$, $Y^3$ and $Y^4$ is individually and independently selected from the group consisting of N and $CR^7$, under the proviso that at least two of $Y^1$, $Y^2$, $Y^3$ and $Y^4$ are $CR^7$,
wherein
each and any of $R^7$ is individually and independently selected from the group consisting of hydrogen, halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido, preferably each and any of $R^7$ is individually and independently selected from the group consisting of methyl and methoxy, more preferably $R^7$ is 5-methoxy or 5-halogen.

Embodiment 17

The compound of embodiment 16, wherein
each and any of $Y^1$, $Y^2$, $Y^3$ and $Y^4$ is $CR^7$.

Embodiment 18

The compound of embodiment 17, wherein
$R^7$ is hydrogen.

Embodiment 19

The compound of any one of embodiments 16 to 18, preferably of any one of embodiments 17 to 18, wherein
$R^4$ is selected from the group consisting of hydrogen, alkyl and benzyl, preferably $R^4$ is hydrogen or methyl, more preferably $R^4$ is hydrogen.

Embodiment 20

The compound of any one of embodiments 16 to 19, preferably any one of embodiments 17 to 19, wherein
R6 is hydrogen or alkyl, preferably hydrogen or methyl, more preferably methyl.

Embodiment 21

The compound of embodiment 16, wherein
each and any of $Y^1$, $Y^2$, $Y^3$ and $Y^4$ is individually and independently selected from the group consisting of N and $CR^7$, under the proviso that one or two of $Y^1$, $Y^2$, $Y^3$ and $Y^4$ are N.

Embodiment 22

The compound of embodiment 21, wherein
$R^7$ is hydrogen.

Embodiment 23

The compound of any one of embodiments 16 and 21 to 22, preferably of any one of embodiments 21 to 22, wherein
$R^4$ is selected from the group consisting of hydrogen, alkyl and benzyl, preferably $R^4$ is hydrogen or methyl, more preferably $R^4$ is hydrogen.

Embodiment 24

The compound of any one of embodiments 16 and 21 to 23, preferably any one of embodiments 21 to 23, wherein $R^6$ is hydrogen or alkyl, preferably hydrogen or methyl, more preferably methyl.

Embodiment 25

The compound of any one of embodiments 1 to 24, preferably any one of embodiments 16 to 24, wherein
$R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 26

The compound of embodiment 25, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 ring atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted phenyl, substituted thiophenyl and substituted pyridinyl.

Embodiment 27

The compound of embodiment 26, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 28

The compound of embodiment 27, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 29

The compound of embodiment 26, wherein each and any of the substituents is individually any independently selected from the group consisting of alkyl, substituted alkyl, alkoxy, substituted alkoxy, alkynly and halogen.

Embodiment 30

The compound of embodiment 29, wherein
alkyl is methyl or ethyl,
substituted alkyl is halogen-substituted methyl or acetyl,
alkoxy is ethoxy, and
alkynyl is vinyl.

Embodiment 31

The compound of any one of embodiments 16 to 26, preferably embodiment 26, wherein the compound is of formula (VI)

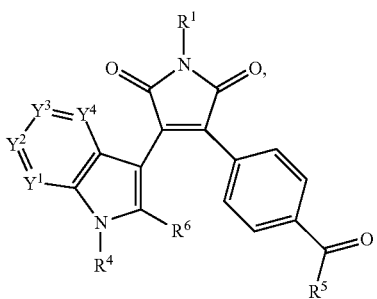

(VI)

wherein R⁵ is selected from the group consisting of alkyl, aminoalkyl, alkoxyalkyl, hydroxyalkyl, aryl and heteroaryl.

Embodiment 32

The compound of any one of embodiments 16 to 26, preferably embodiment 26, wherein the compound is of formula (V)

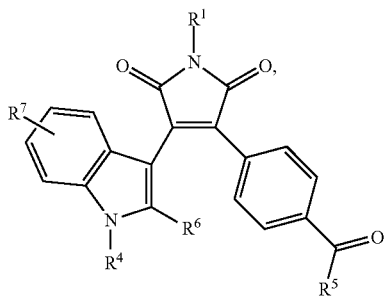

(V)

Embodiment 33

The compound of any one of embodiments 31 and 32, wherein
R⁵ is methyl.

Embodiment 34

The compound of any one of embodiments 1 to 33, wherein the compound is selected from the group consisting of 1-Methyl-3,4-bis-(2-methyl-1H-indol-3-yl)-1H-pyrrole-2,5-dione;
1-Methyl-3-(2-methyl-1H-indol-3-yl)-4-(4-vinylphenyl)-1H-pyrrole-2,5-dione;
1-Methyl-3-(2-methyl-1H-indol-3-yl)-4-phenyl-1H-pyrrole-2,5-dione;
3-(4-Acetylphenyl)-1-methyl-4-(2-methyl-1H-indol-3-yl)-1H-pyrrole-2,5-dione (also referred to herein as PDA-66);
3-(2,6-Dimethylphenyl)-1-methyl-4-(2-methyl-1H-indol-3-yl)-1H-pyrrole-2,5-dione;
3-(3-Chlorophenyl)-1-methyl-4-(2-methyl-1H-indol-3-yl)-1H-pyrrole-2,5-dione;
3-(2,4-Dichlorophenyl)-1-methyl-4-(2-methyl-1H-indol-3-yl)-1H-pyrrole-2,5-dione;
1-Methyl-3-(2-methyl-1H-indol-3-yl)-4-(thiophen-3-yl)-1H-pyrrole-2,5-dione;
1-Methyl-3-(2-methyl-1H-indol-3-yl)-4-(pyridin-4-yl)-1H-pyrrole-2,5-dione;

1-Methyl-3-(2-methyl-1H-indol-3-yl)-4-(naphthalen-2-yl)-1H-pyrrole-2,5-dione;
3-(2,5-Dimethoxyphenyl)-1-methyl-4-(2-methyl-1H-indol-3-yl)-1H-pyrrole-2,5-dione;
1-Methyl-3-(2-methyl-1H-indol-3-yl)-4-(2-(trifluoromethyl)phenyl)-1H-pyrrole-2,5-dione;
3-(4-Fluorophenyl)-1-methyl-4-(2-methyl-1H-indol-3-yl)-1H-pyrrole-2,5-dione;
3-(5-Acetyl-2-fluorophenyl)-1-methyl-4-(2-methyl-1H-indol-3-yl)-1H-pyrrole-2,5-dione;
N-(4-(1-Methyl-4-(2-methyl-1H-indol-3-yl)-2,5-dioxo-2,5-dihydro-1H-pyrrol-3-yl)phenyl) acetamide;
3-(2-Methyl-1H-indol-3-yl)-4-phenylfuran-2,5-dione;
3-(4-Acetylphenyl)-4-(2-methyl-1H-indol-3-yl)-1H-pyrrole-2,5-dione;
3-(2-Methyl-1H-indol-3-yl)-4-(naphthalen-2-yl)furan-2,5-dione;
3-(2-Methyl-1H-indol-3-yl)-4-(naphthalen-2-yl)-1H-pyrrole-2,5-dione;
3-(4-Acetylphenyl)-4-(2-methyl-1H-indol-3-yl)furan-2,5-dione; and
3-(2-Methyl-1H-indol-3-yl)-4-phenyl-1H-pyrrole-2,5-dione Embodiment 35

The compound of any one of embodiments 1 to 34, wherein the compound is 3-(4-acetylphenyl)-4-(2-methyl-1H-indol-3-yl)-1H-pyrrole-2,5-dione

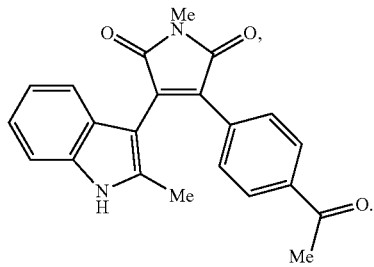

(VII)

Embodiment 36

The compound of any one of embodiments 1 to 34, wherein the compound is 3-(4-acetylphenyl)-1-methyl-4-(2-methyl-1H-indol-3-yl)-1H-pyrrole-2,5-dione

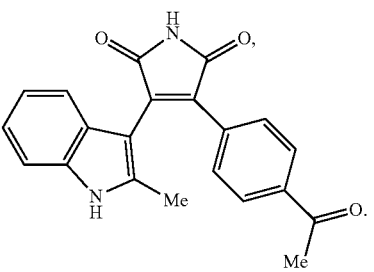

(VIII)

Embodiment 37

A compound of formula (I):

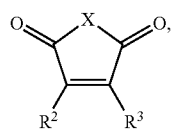

a pharmaceutically acceptable salt thereof, a hydrate thereof, a solvate thereof, a metabolite thereof or a prodrug thereof; wherein X is selected from the group consisting of N—$R^1$, O and S;
$R^1$ is selected from the group consisting of alkyl, cycloalkyl, aryl, arylalkyl and hydrogen;
$R^2$ is selected from the group consisting of indolyl, substituted indolyl, azaindolyl and substituted azaindolyl; and
$R^3$ is selected from the group consisting of aryl, substituted aryl, unsubstituted heteroaryl, heterocyclyl and substituted heterocyclyl.

Embodiment 38

The compound of embodiment 37, wherein
$R^2$ comprises one, two, three, four, five or six substituents, whereby each and any of the substituents is individually and independently selected from the group comprising halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 39

The compound of any one of embodiments 37 to 38, wherein
$R^3$ comprises one, two, three, four, five, six or seven substituents, whereby each and any of the substituents is individually and independently selected from the group comprising hydrogen, alkyl, alkenyl, alkynyl, aryl, acyl, formyl, halogen, haloalkyl, alkylthio, monoalkylamino, dialkylamino, monoarylamino, diarylamino, alkylarylamino, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 40

The compound of any one of embodiments 37-39, wherein
X is N—$R^1$, and wherein
$R^1$ is preferably selected from the group consisting of alkyl, hydrogen, phenyl and benzyl.

Embodiment 41

The compound of embodiment 40, wherein
$R^1$ is selected from the group consisting of methyl, butyl and hydrogen, preferably $R^1$ is selected from the group consisting of methyl and hydrogen.

Embodiment 42

The compound of any one of embodiments 37 to 39, wherein X is O.

Embodiment 43

The compound of any one of embodiments 37 to 42, preferably any one of embodiments 4 to 6, wherein
$R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 44

The compound of embodiment 43, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted indolyl, substituted thiophenyl and substituted pyridinyl.

Embodiment 45

The compound of embodiment 44, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 46

The compound of embodiment 45, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 47

The compound of embodiment 44, wherein $R^3$ is substituted phenyl and each and any of the substituents is individually any independently selected from the group consisting of alkyl, substituted alkyl, alkoxy, substituted alkoxy, alkynly and halogen.

Embodiment 48

The compound of embodiment 47, wherein
alkyl is methyl or ethyl,
substituted alkyl is halogen-substituted methyl or acetyl,
alkoxy is ethoxy, and
alkynyl is vinyl.

Embodiment 49

The compound of embodiment 44, wherein the compound is of formula (IV)

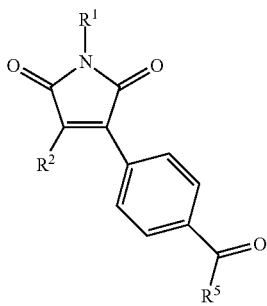

(IV)

wherein $R^5$ is selected from the group consisting of alkyl, aminoalkyl, alkoxyalkyl, hydroxyalkyl, aryl and heteroaryl.

Embodiment 50

The compound of embodiment 49, wherein
$R^5$ is methyl.

Embodiment 51

The compound of any of embodiments 37 to 50, preferably any one of embodiments 1 to 6, more preferably any one of embodiments 4 to 6, wherein each and any of indolyl, substituted indolyl, azaindolyl and substituted azaindolyl of $R^2$ is individually and independently either unprotected or protected at N, preferably at N of the 5-membered ring.

Embodiment 52

The compound of any one of embodiments 37 to 51, preferably any one of embodiments 37 to 42, more preferably any one of embodiments 40 to 42, wherein
$R^2$ is a moiety of formula (VIa)

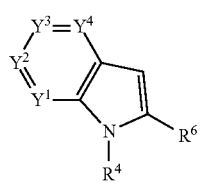

(VIa)

wherein
$R^4$ is selected from the group consisting of hydrogen, aryl, heteroaryl, alkyl, cycloalkyl, polyfluoroalkyl, arylalkyl and heteroarylalkyl,
$R^6$ is selected from the group consisting of alkyl and aryl,
each and any of $Y^1$, $Y^2$, $Y^3$ and $Y^4$ is individually and independently selected from the group consisting of N and $CR^7$, under the proviso that at least two of $Y^1$, $Y^2$, $Y^3$ and $Y^4$ are $CR^7$,
wherein
each and any of $R^7$ is individually and independently selected from the group consisting of hydrogen, halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido, preferably each and any of $R^7$ is individually and independently selected from the group consisting of methyl and methoxy, more preferably $R^7$ is 5-methoxy or 5-halogen.

Embodiment 53

The compound of embodiment 52, wherein
each and any of $Y^1$, $Y^2$, $Y^3$ and $Y^4$ is $CR^7$.

Embodiment 54

The compound of embodiment 53, wherein
$R^7$ is hydrogen.

Embodiment 55

The compound of any one of embodiments 52 to 54, preferably of any one of embodiments 53 to 54, wherein
$R^4$ is selected from the group consisting of hydrogen, alkyl and benzyl, preferably $R^4$ is hydrogen or methyl, more preferably $R^4$ is hydrogen.

Embodiment 56

The compound of any one of embodiments 52 to 55, preferably any one of embodiments 53 to 55, wherein
R6 is hydrogen or alkyl, preferably hydrogen or methyl, more preferably methyl.

Embodiment 57

The compound of embodiment 52, wherein
each and any of $Y^1$, $Y^2$, $Y^3$ and $Y^4$ is individually and independently selected from the group consisting of N and $CR^7$, under the proviso that one or two of $Y^1$, $Y^2$, $Y^3$ and $Y^4$ are N.

Embodiment 58

The compound of embodiment 57, wherein
$R^7$ is hydrogen.

Embodiment 59

The compound of any one of embodiments 52 and 57 to 58, preferably of any one of embodiments 57 to 58, wherein
$R^4$ is selected from the group consisting of hydrogen, alkyl and benzyl, preferably $R^4$ is hydrogen or methyl, more preferably $R^4$ is hydrogen.

Embodiment 60

The compound of any one of embodiments 52 and 57 to 59, preferably any one of embodiments 57 to 59, wherein $R^6$ is hydrogen or alkyl, preferably hydrogen or methyl, more preferably methyl.

Embodiment 61

The compound of any one of embodiments 37 to 60, preferably any one of embodiments 52 to 60, wherein $R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 62

The compound of embodiment 61, wherein $R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 ring atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted phenyl, substituted thiophenyl and substituted pyridinyl.

Embodiment 63

The compound of embodiment 62, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 64

The compound of embodiment 63, wherein $R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 65

The compound of embodiment 62, wherein each and any of the substituents is individually any independently selected from the group consisting of alkyl, substituted alkyl, alkoxy, substituted alkoxy, alkynly and halogen.

Embodiment 66

The compound of embodiment 65, wherein
alkyl is methyl or ethyl,
substituted alkyl is halogen-substituted methyl or acetyl,
alkoxy is ethoxy, and
alkynyl is vinyl.

Embodiment 67

The compound of any one of embodiments 52 to 62, preferably embodiment 62, wherein the compound is of formula (VI)

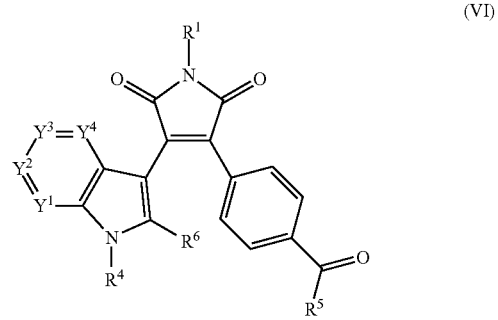

(VI)

wherein $R^5$ is selected from the group consisting of alkyl, aminoalkyl, alkoxyalkyl, hydroxyalkyl, aryl and heteroaryl.

Embodiment 68

The compound of any one of embodiments 52 to 62, preferably embodiment 62, wherein the compound is of formula (V)

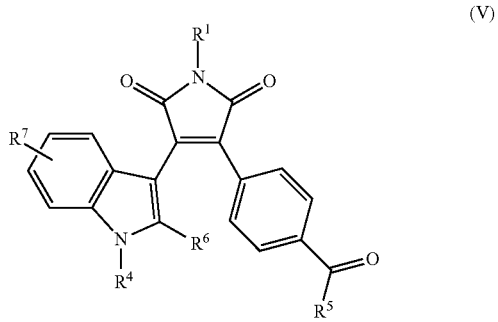

(V)

Embodiment 69

The compound of any one of embodiments 67 and 68, wherein
$R^5$ is methyl.

Embodiment 70

The compound of any one of embodiments 37 to 69, wherein the compound is selected from the group consisting of 1-Methyl-3,4-bis-(2-methyl-1H-indol-3-yl)-1H-pyrrole-2,5-dione;
1-Methyl-3-(2-methyl-1H-indol-3-yl)-4-(4-vinylphenyl)-1H-pyrrole-2,5-dione;
1-Methyl-3-(2-methyl-1H-indol-3-yl)-4-phenyl-1H-pyrrole-2,5-dione;
3-(4-Acetylphenyl)-1-methyl-4-(2-methyl-1H-indol-3-yl)-1H-pyrrole-2,5-dione (also referred to herein as PDA-66);
3-(2,6-Dimethylphenyl)-1-methyl-4-(2-methyl-1H-indol-3-yl)-1H-pyrrole-2,5-dione;
3-(3-Chlorophenyl)-1-methyl-4-(2-methyl-1H-indol-3-yl)-1H-pyrrole-2,5-dione;

3-(2,4-Dichlorophenyl)-1-methyl-4-(2-methyl-1H-indol-3-yl)-1H-pyrrole-2,5-dione;
1-Methyl-3-(2-methyl-1H-indol-3-yl)-4-(thiophen-3-yl)-1H-pyrrole-2,5-dione;
1-Methyl-3-(2-methyl-1H-indol-3-yl)-4-(pyridin-4-yl)-1H-pyrrole-2,5-dione;
1-Methyl-3-(2-methyl-1H-indol-3-yl)-4-(naphthalen-2-yl)-1H-pyrrole-2,5-dione;
3-(2,5-Dimethoxyphenyl)-1-methyl-4-(2-methyl-1H-indol-3-yl)-1H-pyrrole-2,5-dione;
1-Methyl-3-(2-methyl-1H-indol-3-yl)-4-(2-(trifluoromethyl)phenyl)-1H-pyrrole-2,5-dione;
3-(4-Fluorophenyl)-1-methyl-4-(2-methyl-1H-indol-3-yl)-1H-pyrrole-2,5-dione;
3-(5-Acetyl-2-fluorophenyl)-1-methyl-4-(2-methyl-1H-indol-3-yl)-1H-pyrrole-2,5-dione;
N-(4-(1-Methyl-4-(2-methyl-1H-indol-3-yl)-2,5-dioxo-2,5-dihydro-1H-pyrrol-3-yl)phenyl) acetamide;
3-(2-Methyl-1H-indol-3-yl)-4-phenylfuran-2,5-dione;
3-(4-Acetylphenyl)-4-(2-methyl-1H-indol-3-yl)-1H-pyrrole-2,5-dione;
3-(2-Methyl-1H-indol-3-yl)-4-(naphthalen-2-yl)furan-2,5-dione;
3-(2-Methyl-1H-indol-3-yl)-4-(naphthalen-2-yl)-1H-pyrrole-2,5-dione;
3-(4-Acetylphenyl)-4-(2-methyl-1H-indol-3-yl)furan-2,5-dione; and
3-(2-Methyl-1H-indol-3-yl)-4-phenyl-1H-pyrrole-2,5-dione

Embodiment 71

The compound of any one of embodiments 37 to 70, wherein the compound is 3-(4-acetylphenyl)-4-(2-methyl-1H-indol-3-yl)-1H-pyrrole-2,5-dione

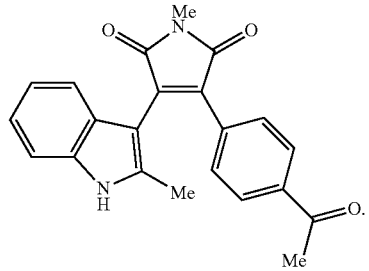

(VII)

Embodiment 72

The compound of any one of embodiments 37 to 70, wherein the compound is 3-(4-acetylphenyl)-1-methyl-4-(2-methyl-1H-indol-3-yl)-1H-pyrrole-2,5-dione

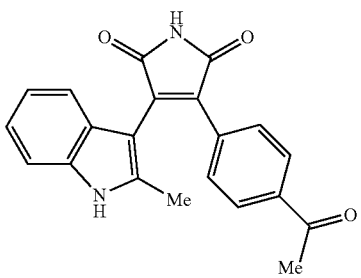

(VIII)

Embodiment 73

The compound of any one of embodiments 37 to 72, wherein R3 is different from indolyl and/or substituted indolyl.

Embodiment 74

The compound of any one of embodiments 1 to 36, wherein cancer is selected from the group comprising breast cancer, lung cancer, including non-small cell lung carcinoma, renal cancer, colon cancer, myelodysplastic syndrome, genitourinary cancer, gastrointestinal cancer, epidermoid cancer, melanoma, glioma, ovarian cancer, pancreatic cancer, lymphoma, myeloma, colorectal cancer, neuroblastoma, head and/or neck cancer, bladder cancer, brain cancer in a broader sense and gastric cancer in a broader sense, any metastases of any thereof.

Embodiment 75

The compound of any one of embodiments 1 to 36, wherein cancer is breast cancer and metastases.

Embodiment 76

The compound of any one of embodiments 1 to 36, wherein wherein cancer is lung cancer, including non-small cell lung cancer, and metastases thereof.

Embodiment 77

The compound of any one of embodiments 1 to 36, wherein cancer is renal cancer and metastases thereof.

Embodiment 78

The compound of any one of embodiments 1 to 36, wherein cancer is colon cancer and metastases thereof.

Embodiment 79

The compound of any one of embodiments 1 to 36, wherein cancer is myelodysplastic syndrome and metastases thereof.

Embodiment 80

The compound of any one of embodiments 1 to 36, wherein genitourinary cancer and metastases thereof.

Embodiment 81

The compound of any one of embodiments 1 to 36, wherein cancer is gastrointestinal cancer and metastases thereof.

Embodiment 82

The compound of any one of embodiments 1 to 36, wherein cancer is epidermoid cancer and metastases thereof.

Embodiment 83

The compound of any one of embodiments 1 to 36, wherein cancer is melanoma and metastases thereof.

Embodiment 84

The compound of any one of embodiments 1 to 36, wherein cancer is glioma and metastases thereof.

Embodiment 85

The compound of any one of embodiments 1 to 36, wherein cancer is ovarian cancer and metastases thereof.

Embodiment 86

The compound of any one of embodiments 1 to 36, wherein cancer is pancreatic cancer and metastases thereof.

Embodiment 87

The compound of any one of embodiments 1 to 36, wherein cancer is lymphoma and metastases thereof.

Embodiment 88

The compound of any one of embodiments 1 to 36, wherein cancer is myeloma and metastases thereof.

Embodiment 89

The compound of any one of embodiments 1 to 36, wherein cancer is colorectal cancer and metastases and thereof.

Embodiment 90

The compound of any one of embodiments 1 to 36, wherein cancer is neuroblastoma and metastases thereof.

Embodiment 91

The compound of any one of embodiments 1 to 36, wherein cancer is head and/or neck cancer and metastases thereof.

Embodiment 92

The compound of any one of embodiments 1 to 36, wherein cancer is bladder cancer and metastases thereof.

Embodiment 93

The compound of any one of embodiments 1 to 36, wherein cancer is brain cancer and metastases thereof.

Embodiment 94

The compound of any one of embodiments 1 to 36, wherein cancer is gastric neck cancer and metastases thereof.

Embodiment 95

The compound of any one of embodiments 1 to 36 and 74 to 94, wherein the method comprises the administration of a second therapeutic agent, wherein the second therapeutic agent is a chemotherapeutic agent.

Embodiment 96

The compound of embodiment 95, wherein the chemotherapeutic agent is selected from the group comprising cytarabine, etoposide, mitoxantron, cyclophosphamide, retinoic acid, daunorubicin, doxorubicin, idarubicin, azacytidine, decitabine, a tyrosin-kinase inhibitor, a antineoplastic antibody, vincaalkaloids and steroids.

Embodiment 97

The compound of embodiment 96, wherein the chemotherapeutic agent is a tyrosin-kinas inhibitor, wherein the tyrosin-kinase inhibitor is selected from the group comprising sorafenib, dasatinib, nilotinib, nelarabine and fludarabine.

Embodiment 98

The compound of embodiment 96, wherein the chemotherapeutic agent is Alemtuzumab (Campath®)

Embodiment 99

Use of compounds according to any one of embodiments 1 to 73 for the manufacture of a medicament against cancer.

Embodiment 100

A pharmaceutical compositions comprising a compound of any one of embodiments 1 to 73 and a pharmaceutically acceptable carrier or excipient.

Embodiment 101

The pharmaceutical composition of embodiment 100, wherein the pharmaceutical composition comprises a second therapeutic agent, wherein the second therapeutic agent is a chemotherapeutic agent.

Embodiment 102

A method of treatment and/or prevention of cancer, wherein the method comprises administering to a subject in need thereof an therapeutically effective amount of a compound of any one of embodiments 1 to 73 or of a pharmaceutical composition of any one of embodiments 100 to 101.

The present invention is based on the surprising finding that that the compound of the invention is capable of inhibition GSK3β. More specifically, the present invention is based on the surprising finding that the compound of the invention is suitable for the treatment of cancer. Based on this finding, the compound of the invention may be used in the treatment of any disease involving GSK3β. In an embodiment cancer is such disease involving GSK3β, whereby cancer is preferably is any one of breast cancer, lung cancer, including non-small cell lung carcinoma, renal cancer, colon cancer, myelodysplastic syndrome, genitourinary cancer, gastrointestinal cancer, epidermoid cancer, melanoma, glioma, ovarian cancer, pancreatic cancer, lymphoma, myeloma, colorectal cancer, neuroblastoma, head and/or neck cancer, bladder cancer, brain cancer in a broader sense and gastric cancer in a broader sense.

In an embodiment of the compound of the invention the indolyl, substituted indolyl, azaindolyl and substituted azaindolyl are each and individually attached to the maleimide moiety via a 3'-position of the indolyl and azaindolyl, respectively.

In an embodiment of the invention the indolyl, substituted indolyl, azaindolyl and substituted azaindolyl are each and individually attached to the maleimide moiety via a 3'-position of the indolyl and azaindolyl, respectively, A compound of the invention may exist in free or in salt form and/or solvate form or of the salt thereof. A "pharmaceutically acceptable salt" of a compound relates to a salt that is pharmaceutically acceptable and that possesses the desired pharmacological activity of the parent compound. "Physiologically or pharmaceutically acceptable salts" of a compounds of the invention include but are not limited to acid addition salts with a) inorganic acids, such as, for example, hydrochloric acid, hydrobromic acid, sulfuric acid, nitric acid or phosphoric acid and the like, or formed with b) organic acids, including but not limited to carboxylic acids, such as, e.g., acetic acid, tartaric acid, lactic acid, citric acid, maleic acid, malonic acid, succinic acid, ascorbic acid, fumaric acid, cinnamic acid, mandelic acid, benzoic acid, gluconic acid and the like, or c) sulfonic acids, such as, e.g., methane sulfonic acid, benzene sulfonic acid, toluene sulfonic acid, camphorsulfonic acid and the like.

Physiologically acceptable solvates are preferably hydrates.

Unless otherwise stated, the following terms used in the specification and claims have, in a preferred embodiment, the meanings given below:

The terms "alkyl" and "alkyloxy" as preferably used herein or in combination with other terms means linear or branched hydrocarbon structures and combinations thereof with one, two, three, four, five or six carbon atoms, including but not limited to, e. g., methyl, ethyl, propyol (iso-, n-), butyl (iso-, n-, tert-), pentyl, hexyl, methoxy, ethoxy, propoxy (iso-, n-), butoxy (iso-, n-, tert-), pentoxy, hexoxy and the like.

As preferably used herein the term "cycloalkyl" means mono- or polycyclic saturated or unsaturated three, four, five, six or seven ring carbocyclic alkyl groups, including but not limited to cyclopropyl, cyclobutyl, cyclopentyl, cyclohexyl, cycloheptyl, cyclobutenyl, cyclopentenyl, cyclopentadienyl, cyclohexyl, cyclohexenyl, cyclohexadienyl, cycloheptenyl, cycloheptadienyl and cycloheptatrienyl and the like.

The term "aryl" as preferably used herein means mono- and polycyclic aromatic groups having 6, 7, 8, 9, 10, 11, 12, 13 or 14 backbone carbon atoms, optionally fused to a carbocyclic group, including but not limited to phenyl, naphthyl, indenyl, indanyl, azulenyl, fluorenyl, 1,2,3,4-tetrahydronaphthyl, phenanthrenyl and the like.

The term "monoalkylamino" or "monoarylamino" as preferably used herein means a radical —NHR where R is an alkyl, cycloalkyl or aryl as defined herein, including but not limited to, e. g., methylamino, cyclohexylamino, phenylamino and the like.

The term "dialkylamino" or "diarylamino" as preferably used herein means a radical —NRR', where each of R and R' individually and independently represents an alkyl, cycloalkyl or aryl as defined herein, including but not limited to, e. g, dimethylamino, dicyclohexylamino, methylethylamino, diphenylamino and the like.

The term "alkylthio" or "arylthio" as preferably used herein means a radical —SR where R is an alkyl or aryl as defined herein, including but not limited to, e. g., methylthio, ethylthio, propylthio, butylthio, phenylthio and the like.

The term "acylamino" as preferably used herein means a radical-NR'C(O)R, where R' is hydrogen or alkyl, and R is hydrogen, alkyl, cycloalkyl, cycloalkylalkyl, phenyl or phenylalkyl, wherein alkyl, cycloalkyl, cycloalkylalkyl, and phenylalkyl are as defined herein. Representative examples include, but are not limited to, formylamino, acetylamino, cylcohexylcarbonylamino, benzoylamino and the like.

The term "haloalkyl" as preferably used herein means substituted alkyl as defined herein, wherein alkyl is substituted with one or more of same or different halogen atoms, including but not limited to, e. g., —CH$_2$Cl, —CF$_3$, —CH$_2$CF$_3$, —CH$_2$CCl$_3$ and the like.

The terms "alkylsufinyl" and "arylsulfinyl" as preferably used herein mean a —S(O)R group, where R is alkyl (in case of alkylsulfinyl) and aryl (in case of arylsulfinyl) as defined herein, including but not limited to, e.g., methylsulfinyl, ethylsulfinyl, propylsulfinyl, butylsulfinyl, each including all isomeric forms thereof, and the like.

The terms "alkylsulfonyl" and "arylsulfonyl" as preferably used herein mean a —S(O)$_2$R group, where R is alkyl (in case of alkylsulfonyl) and aryl (in case of arylsulfonyl) as defined herein, including but not limited to, e.g., methylsulfonyl, ethylsulfonyl, propylsulfonyl, butylsulfonyl, each including all isomeric forms thereof, and the like.

The terms "alkylsulfinamido" and arylsulfinamido" as preferably used herein mean a —S(O)NRR' group, where R and R' are hydrogen and/or alkyl (in case of alkylsulfinamido) and aryl (in case of arylsulfinamido) as defined herein, including but not limited to, e.g., tert-butanesulfinamide, p-toluenesulfinamide and the like.

The terms "alkylsulfonamido" and "arylsulfonamido" as preferably used herein mean a —S(O)$_2$NRR' group, where R and R' are hydrogen and/or alkyl (in case of alkylsulfonamido) and aryl (in case of arylsulfonamido) as defined herein, including but not limited to, e.g., methansulfonamide and the like.

The term "heteroaryl" as preferably used herein means mono- or bi-carbocyclic aromatic groups with 1, 2, 3 or 4 ring-heteroatoms selected from N, S and O. Preferably, a total number of ring atoms is 5, 6, 7, 8, 9 or 10. Examples without limitation of heteroaryl groups are benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolynyl, purinyl, carbazolyl, benzoxazolyl, benzamidazolyl, indolyl, isoindolyl, diazinyl, pyrazinyl, triazinyl, tetrazinyl, tetrazolyl, benzothiophenyl, benzopyridyl, benzimidazolyl and derivatives thereof. The heteroaryl ring is optionally substituted independently with one or more substituents, wherein each and any substituent is individually and independently selected from alkyl, haloalkyl, heteroalkyl, alkoxy, hydroxy, halogen, nitro, cyano groups and the like, preferably as defined herein.

The term "heterocyclyl" as preferably used herein means a mono- or polycyclic saturated or unsaturated non-aromatic heterocyclyl groups of 5, 6, 7 or 8 ring atoms in which one or two ring atoms are heteroatoms selected from NR (where R is independently hydrogen or alkyl, preferably as defined herein), O, or S(O)$_n$ (where n is an integer from 0, 1 and 2), the remaining ring atoms being carbon atoms, where one or two carbon atoms may optionally be replaced by a carbonyl group. The heterocyclyl ring may be optionally substituted independently with one, two or three substituents, wherein each substituent is individually and independently selected from alkyl, haloalkyl, heteroalkyl, halogen, nitro, cyano, hydroxy, alkoxy, amino, mono- or dialkylamino, acyl, preferably as defined herein. Examples for heterocyclyl groups include but are not limited to tetrahydropyranyl, tetrahydropyranyl, imidazolinyl, imidazolidinyl, pyrrolidinyl, piperidinyl, piperazinyl, morpholinyl, thiomorpholinyl, N-methylpiperidin-3-yl, N-methylpyrrolidin-3-yl, pyrrolinyl and derivatives of each thereof.

The term "halogen" as preferably used herein means a halogen atom selected from fluorine, chlorine, bromine and iodine, preferably the halogen atom is either fluorine or chlorine, more preferably the halogen atom is fluorine.

The term "protected" as preferably used herein means those organic groups intended to protect nitrogen atoms against undesirable reactions during synthetic procedures. Suitable nitrogen protecting groups are well known in the art and include but are not limited to, e. g., trimethylsilyl, tert-butyldimethylsilyl (TBDMS), benzyl, benzyloxycarbonyl (Cbz), 9-fluorenylmethoxycarbonyl (Fmoc), tert-butoxycrbonyl (Boc), trifluoroacetyl, 2-trimethylsilylethanesulfonyl (SES), and the like. Other suitable nitrogen protecting groups which are suitable for the practicing of the invention can be found in the publication of T. W. Greene and G. M. Wuts, "Protecting Groups in Organic Synthesis", Second Edition, Wiley, New York, 1991, and references cited therein.

In an embodiment and as preferably used herein, a disease involving GSK3β is a disease where cells expressing GSK3β and tissue expressing GSK3β, respectively, are either a or the cause for the disease and/or the symptoms of the disease, or are part of the pathology underlying the disease. In an embodiment of the disease, preferably when used in connection with the treatment, treating and/or therapy of the disease, affecting the cells, the tissue and pathology, respectively, results in cure, treatment or amelioration of the disease and/or the symptoms of the disease.

Numerous additional aspects and advantages of the invention will become apparent to those skilled in the art upon consideration of the following detailed description of the invention which describes presently preferred embodiments thereof.

The invention also relates to the metabolites and prodrugs of the compound of the invention. Preferably, a prodrug of a compound of the invention is prepared by modifying functional groups present in the compound of the invention in such a way that the modifications may be cleaved in vivo to release a or the active compound. Preferably, such active compound is a compound of the invention or a compound derived therefrom having at least one characteristic of a compound of the invention. Preferably, such characteristic is the capacity to inhibit GSK3β and/or the suitability for the treatment of a GKS3b involving disease, preferably cancer.

In accordance therewith the term "prodrug" refers to (a) an inactive form of a drug that exerts its effects after metabolic processes in vivo, when such prodrug is administered to a mammalian subject, to release an active parent drug and preferably a compound of the invention, or (b) a substance that gives rise to a pharmacologically active metabolite, although not itself active (i.e. an inactive precursor). Examples of prodrugs include, but are not limited to esters, carbamates and the like.

As preferably used herein the term "metabolite" refers to a) a product of metabolism, including an intermediate and an end product, b) any substance in metabolism (either as product of metabolism or as necessary for metabolism), or c) any substance produced or used during metabolism. More preferably, the term "metabolite" refers to an end product that remains after metabolism.

As preferably used herein, the term "pharmaceutically acceptable excipient" an excipient that is useful in preparing a pharmaceutical composition that is generally safe, non-toxic and neither biologically nor otherwise undesirable, or adversely affects the therapeutic benefit of the compound of the invention. A "pharmaceutically acceptable excipient" as preferably used in the specification and claims includes both one and more than one such excipient. Such excipient may be any solid, liquid, semi-solid. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e. g., peanut oil, soybean oil, mineral oil, sesame oil, and the like.

As preferably used herein, the term "therapeutically effective amount" means the amount of a compound of the invention formula (I) that, when administered to a mammal for treating a disease, is sufficient to effect such treatment for the disease. The "therapeutically effective amount" will vary depending on the compound, the disease and its severity and the age, weight, etc., of the mammal to be treated.

As preferably used herein, "treating" or "treatment" of a disease includes: (1) preventing the disease, i. e. causing the clinical symptoms of the disease not to develop in a mammal that may be exposed to or predisposed to the disease but does not yet experience or display symptoms of the disease, (2) inhibiting the disease, i. e., arresting or reducing the development of the disease or its clinical symptoms, or (3) relieving the disease, i. e., causing regression of the disease or its clinical symptoms.

The term "treatment of cancer" includes partial or total inhibition of cancer in a subject, as well as partial or total destruction of the cancer cells.

As preferably used herein, the term "prevention of cancer" includes preventing the onset of clinically evident cancer as well as preventing the onset of a preclinical evident stage of cancer in subjects at risk.

In an embodiment of the invention, cancer is a solid cancer and metastases thereof. In a preferred embodiment, cancer is selected from the group comprising breast cancer, lung cancer, including non-small cell lung carcinoma, renal cancer, colon cancer, myelodysplastic syndrome, genitourinary cancer, gastrointestinal cancer, epidermoid cancer, melanoma, glioma, ovarian cancer, pancreatic cancer, lymphoma, myeloma, colorectal cancer, neuroblastoma, head and/or neck cancer, bladder cancer, brain cancer in a broader sense and gastric cancer in a broader sense, including metastases of any one thereof.

In an embodiment of the invention, cancer is resistant cancer and in particular multidrug resistant cancer, i.e., the cancer cells exhibit resistance to conventional chemotherapeutics, preferably the MDR (multidrug resistance) phenotype; preferably, such resistant cancer is selected from the group comprising breast cancer, lung cancer, including non-small cell lung carcinoma, renal cancer, colon cancer, myelodysplastic syndrome, genitourinary cancer, gastrointestinal cancer, epidermoid cancer, melanoma, glioma, ovarian cancer, pancreatic cancer, lymphoma, myeloma, colorectal cancer, neuroblastoma, head and/or neck cancer, bladder cancer, brain cancer in a broader sense and gastric cancer in a broader sense.

In an embodiment, the compound of the invention is a compound, a physiologically acceptable salt thereof or a physiologically acceptable solvate thereof, which is capable of stimulating apoptosis in cancer cells.

The present invention thus also relates to the use of a compound of the invention, a physiologically acceptable salt or solvate thereof, preferably as defined herein, in combination with one or more than one further chemotherapeutic agent.

In an embodiment of the invention, the treatment of the subject comprises further stimulation of cell death by a conventional method or combination of conventional methods. The conventional methods preferably being selected from the group consisting of irradiation, e. g. external irradiation or administration of radioactive compounds, bone marrow transplantation and treatment with a chemotherapeutic agent which is including antineoplastic agents, multidrug resistance reversing agents, and biological response modifiers, and combinations thereof.

The present invention thus also relates to the use of a compound of the invention, a physiologically acceptable salt or a solvate thereof, preferably as defined herein, in combination with one or more than one further chemotherapeutic agent. Suitable antineoplastic agents may be selected from the group comprising asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, lomustine, mechlorethamine, melphalan, mercaptopurine, methotrexate, mitomycin, mitoxantrone, pentostatin, procarbazine, 6-thioguanine, topotecan, vinblastine, vincristine, dexamethasone, retinoic acid and prednisone. Preferred examples for antineoplastic agents to be used in the treatment of cancer in accordance with the present invention, especially in the treatment of AML or ALL, comprise cytarabine, etoposide, mitoxantron, cyclophosphamide, retinoic acid, daunorubicin, doxorubicin and idarubicin.

When the compounds of formula (I), physiologically acceptable salts or solvates thereof are to be used as active ingredients in the uses, methods and compositions of the present invention, they can be incorporated into standard pharmaceutical dosage forms, which the skilled artisan is familiar with. Basically, any pharmaceutical dosage form may be used in the invention.

The present invention thus also relates to a pharmaceutical composition comprising a pharmaceutically acceptable auxiliary agent in addition to a compound of the invention, a physiologically acceptable salt or solvate thereof as defined above. Such auxiliary agents are known in the art. e. g., the usual pharmaceutical excipients, diluents and adjuvants, e.g., organic and inorganic inert carrier materials such as water, gelatine, lactose, starch, magnesium stearate, talc, vegetable oils, gums, polyalkylene glycols, etc. These pharmaceutical preparations can be employed in a solid form, e.g., as tablets, capsules, or they can be administered in liquid form, e.g., as solutions, suspensions or emulsions.

Further pharmaceutical excipients and adjuvants which may be added to a pharmaceutical composition, include preservatives, antioxidants, antimicrobial agents and other stabilizers; wetting, emulsifying and suspending agents, and anti-caking compounds; fragrance and coloring additives; compositions for improving compressibility, or agents to create a delayed, sustained or controlled release of the active ingredient; and various salts to change the osmotic pressure of the pharmaceutical preparation or to act as buffers. Such excipients and adjuvants are known to the skilled artisan.

It will be acknowledged by a person skilled in the art that a or the compound of the invention is any compound disclosed herein, including but not limited to any compound described in any of the above embodiments and any of the following embodiments.

It will be acknowledged by a person skilled in the art that a or the method of the invention is any method disclosed herein, including but not limited to any method described in any of the above embodiments and any of the following embodiments.

It will be acknowledged by a person skilled in the art that a or the composition of the invention is any composition disclosed herein, including but not limited to any composition described in any of the above embodiments and any of the following embodiments.

As to the synthesis of the compound of the invention a person skilled in the art will acknowledge the following. Disubstituted maleimide and particularly bisindolylmaleimide subunit is present in a number of biologically active compounds. Among these arcyriarubins (Scheme 1; a) represent the simplest members of the naturally occurring 3,4-bisindolylmaleimides. They are structurally related to the arcyriaflavines (b) and to the aglycon of well-known staurosporine (c), rebeccamycine (d) and other biologically active metabolites.

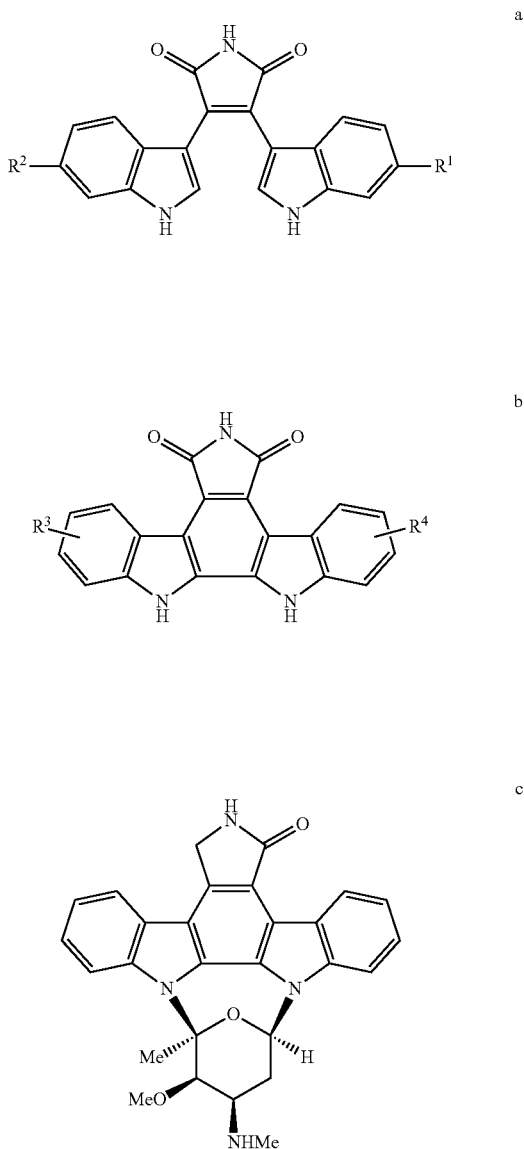

Scheme 1.

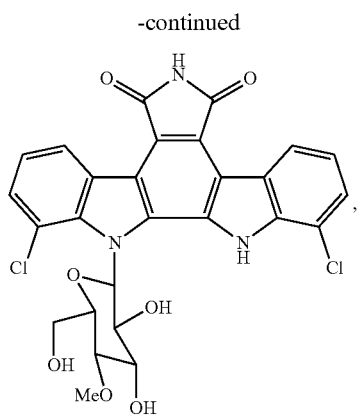

Arcyriarubins (a), arcyriaflavins (b), staurosporine (c), and rebeccamycine (d)

Interestingly, synthetic analogues possess wide spectra of antibacterial, antiviral, antimicrobial and antigenic activities. Furthermore, derivatives of this class of compounds are promising agents for autoimmune diseases, like diabetes and cancer, as well as valuable inhibitors of different protein kinases, especially PKC, which plays an important role in many signal transduction pathways, or GSK3β, therefore, may be used for the treatment of GSK3β mediated diseases. Notably, some derivatives are currently evaluated in human clinical trails as anticancer drugs. For example, Enzastaurin, which is developed by Eli Lilly and Company, is a synthetic bisindolylmaleimide derivative with potential antineoplastic activity and can be used for the treatment of solid tumors (WO02/02094, WO02/02116, and IL165747). In January 2009 Enzastaurin was in the phase III of the clinical trials. This agent may decrease tumor blood supply, preventing its growth. Ruboxistaurin, another bisindolylmaleimid, is an investigational drug for diabetic peripheral retinopathy, was also developed by Eli Lilly, and is presently in a phase III study. Ruboxistaurin is an inhibitor of PKC-beta. Other examples of indolylmaleimide agents have been described in WO2009/071620 and WO 2006/061212. Namely, certain 3-(indolyl)- or 3-(azaindolyl)-4-arylmaleimide derivatives act as angiogenesis inhibitors therefore were proposed their use for controlling angiogenesis and/or vascular dysfunction as well as for treatment of cancer.

Obviously, it is very important to develop new strategies to the new derivatives of this class of bioactive compounds that would show more improved properties, such as enhanced bioavailability, increased metabolic stability, and improved selectivities toward action targets that they can be used as targeted drugs.

As a result of pharmaceutical importance of 3,4-bisindolylmaleimides, a variety of approaches have been reported in the literature for their synthesis. The most widely used methods were developed by groups of W. Steglich (Tetrahedron, 1988, 44, 2887) and M. Faul (JOC, 1998, 63, 6053). Both methods allow the synthesis of symmetrically and unsymmetrically di-substituted maleimides. According to the Steglich procedure indolyl magnesium bromide reacts with 3,4-dibromomaleimide to give mono- or di-substituted products. The outcome of this reaction is strongly dependent on the solvent. The procedure of Faul et al. involves a one step condensation of substituted (aryl or indolyl) acetamides with substituted (aryl or indolyl) glyoxyl esters in the presence of strong base.

Several indolylmaleimide compounds can be also prepared according to the known methods, which are disclosed, for example in WO02/38561, EP328026, WO03/095452 and WO2006/061212.

Selected compounds of this invention were prepared according to the reference "Org. Biomol. Chem. 2008, 6, 992". Typically in a two step sequence first was synthesized 3-halo-4-indolyl- or azaindolylmaleimide derivative, starting from commercially available indole or azaindole derivative and 3,4-dihalomaleimide. In particular case 2-methylindole (1) reacted with 3,4-dibromomaleimide (2) to form 3-bromo-1-methyl-4-(2-methyl-3-indolyl)-maleimide (3) (Scheme 2).

Scheme 2

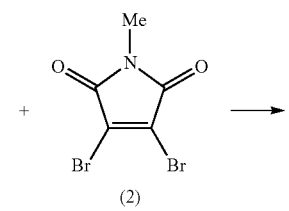

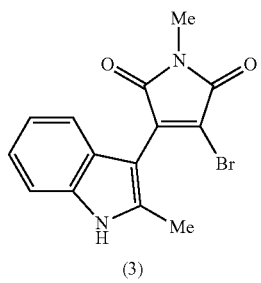

Using Grignard reagent according to the protocol of Steglich led to the desired mono-substituted product in 68% isolated yield. In addition, a minor amount of the corresponding di-substituted product (5%) was isolated. However, applying the modification of Ohkubo (Tetrahedron, 1996, 52, 8099), which means metallation of indole with lithium hexamethyldisilazane (LiHMDS) and further reaction with one equivalent of dibromo compound 2, led to 3-bromo-1-methyl-4-(2-methyl-3-indolyl)-maleimide (3) in excellent selectivity and nearly quantitative yield (98%).

Aryl, heteroaryl or heterocyclyl substituents were introduced in the 4-position of maleimide moiety using Suzuki coupling reaction of compound 3 with various substituted or non substituted aryl, heteroaryl or heterocyclyl boronic acids. The coupling reactions were preferably performed in the presence of 0.05 to 4 mol % $Pd(OAc)_2$ and suitable phosphine ligand. Depend on steric and electronic factors good to excellent yield of the corresponding product of formula (I) was obtained. For example, Suzuki coupling reaction of 3-bromo-1-methyl-4-(2-methyl-3-indolyl)-maleimide (3) with phenylboronic acid (4) led to 1-methyl-3-(2-methyl-1H-indol-3-yl)-4-phenyl-1H-pyrrole-2,5-dione (5) in quantitative yield (Scheme 3).

Scheme 3

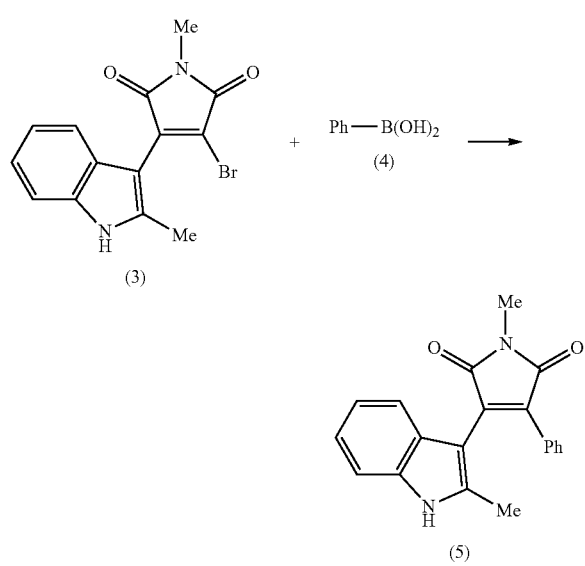

All coupling products are bright colored, stabile crystalline compounds. The resulting 3-indolyl-4-aryl(heteroaryl or heterocyclyl)maleimides constitute new biologically active compounds. Protection and deprotection steps of indole nitrogen are not necessary.

As will be apparent to a person skilled in the art, compound of formula (I) wherein X is N—$R^1$, can be converted to other compound of formula (III) (Scheme 4).

Scheme 4

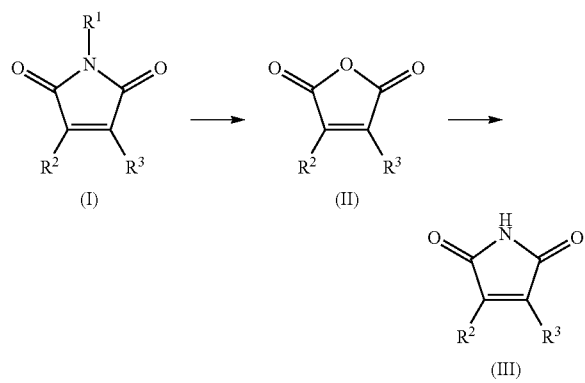

For example, treatment of at maleimide moiety protected compound of formula (I) with strong base, such as sodium or potassium hydroxide led to the formation of corresponding cyclic anhydrides of formula (II), which are easily converted to unprotected compounds of formula (III) over heating with ammonium acetate.

Both conversions proceed in high to excellent yields. Also these products are bright colored, stabile crystalline compounds.

The present invention is now further illustrated by reference to the following figures and examples from which further advantages, features, and embodiments may be taken, wherein FIG. 1 shows two diagrams indicating cell number over time when exposed to compound PDA-66 or control (left panel) and viability of cells when exposed to compound PDA-66 or control (right panel);

EXAMPLES

Figure 1:
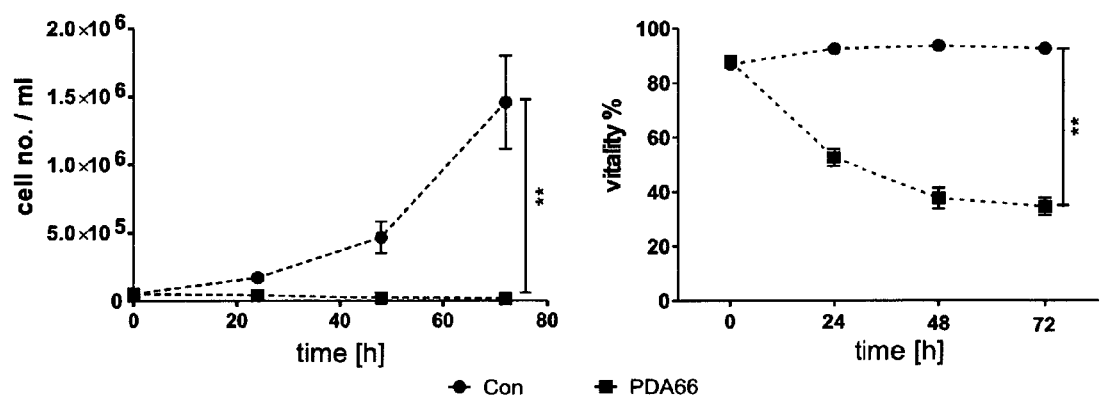

Abbreviations used in general procedures and examples are defined as follows: "HCl" for hydrochloric acid, "KOH" for potassium hydroxide, "NaHCO₃" for sodium hydrocarbonate, "$K_2CO_3$" for potassium carbonate, "$Na_2SO_4$" for sodium sulfate, "$CH_2Cl_2$" for methylene chloride, "THF" for tetrahydrofuran, "EA" for ethyl acetate, "DMSO" for dimethylsulfoxide, "$CDCl_3$" for deuterated chloroform, "TLC" for thin layer chromatography, "LiHMDS" for lithium hexamethyldisilazane, "Pd(OAc)₂" for palladium acetate.

All reactions were carried out under argon atmosphere. Reactions were monitored by TLC analysis (pre-coated silica gel plates with fluorescent indicator UV254, 0.2 mm) and visualized with 254 nm UV light or iodine. Chemicals were purchased from Aldrich, Fluka, Acros, AlfaAsar, Strem and unless otherwise noted were used without further purification. All compounds were characterized by ¹H NMR, ¹³C NMR, GC-MS, HRMS and IR spectroscopy. ¹H spectra were recorded on Bruker AV 300 and AV 400 spectrometers. ¹³C NMR and ¹⁹F NMR spectra were recorded at 75.5 MHz and 282 MHz respectively. Chemical shifts are reported in ppm relative to the center of solvent resonance. Melting points were determined on a digital SMP3 (Stuart). IR spectra were recorded on FT-IR ALPHA (Bruker) with Platinum-ATR (Bruker). EI (70 eV) mass spectra were recorded on MAT 95XP (Thermo ELECTRON CORPORATION). GC was performed on Agilent 6890 chromatograph with a 30 m HP5 column. HRMS was performed on MAT 95XP (EI) and Agilent 6210 Time-of-Flight LC/MS (ESI). GC-MS was performed on Agilent 5973 chromatograph Mass Selective Detector. All yields reported refer to isolated yields.

Example 1: Preparation 1—General Procedure for Condensation of Indole or Azaindoles Derivative with 3,4-Dihalomaleimide Compound and Specific Compounds The (aza)indole derivative (10 mmol) was dissolved in dry THF (20 ml) and cooled under Argon to −20° C., before 21 ml of LiHMDS (1 M in THF) were slowly added. After stirring for 2 h at −20° C., a solution of 3,4-dihalomaleimide derivative (10 mmol) in THF (20 ml) was added to the lithiated (aza)indole solution all at once via syringe. After stirring additional 1 h at −20° C. (TLC control), the reaction mixture was carefully neutralized with 2N aq HCl and extracted with ethyl acetate (3×). The combined organics were washed with sat. aq NaHCO$_3$, brine, and water. After drying over Na$_2$SO$_4$ and concentration, the crude material was crystallized from ether.

Example 1.1

3-Bromo-1-methyl-4-(2-methyl-1H-indol-3-yl)-1H-pyrrole-2,5-dione

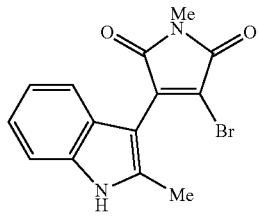 [SMILES: Cc1[nH]c2ccccc2c1C1=C(Br)C(=O)N(C)C1=O]

Orange crystals; $^1$H NMR (CDCl$_3$) δ 2.48 (s, 3H), 3.19 (s, 3H), 7.18 (ddd, 1H), 7.20 (ddd, 1H), 7.31 (ddd, 1H), 7.48 (m, 1H), 8.48 (br.s, 1H); $^{13}$C NMR (CDCl$_3$) δ 14.3, 24.9, 102.0, 110.8, 120.5, 120.7, 120.8, 122.4, 126.4, 135.5, 137.6, 139.3, 166.4, 169.1; GC-MS (EI, 70 eV): m/z (%) 318 (100) [M$^+$], 320 (96) [M$^+$]; HRMS (EI): Cacld for C$_{14}$H$_{11}$O$_2$N$_2$Br: 317.99984. found: 317.99979; IR (ATR, cm$^{-1}$): 3361, 3066, 1771, 1703, 1623, 1422, 1379, 990, 806, 749, 733, 656.

Example 1.2

3-Bromo-1-methyl-4-(1H-pyrrolo[2,3-b]pyridin-3-yl)-1H-pyrrole-2,5-dione

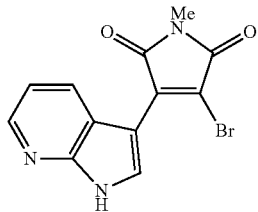 [SMILES: CN1C(=O)C(Br)=C(c2c[nH]c3ncccc23)C1=O]

Preparation was performed using Grignard reagent. Orange crystals; $^1$H NMR (DMSO-d$_6$) δ 2.99 (s, 3H), 7.21 (ddd, 1H, J~3.83, 5.31, 7.36 Hz), 8.20 (s, 1H), 8.31 (dd, 1H, J=1.53, 3.52 Hz), 8.33 (s, 1H), 12.68 (br.s, 1H); $^{13}$C NMR (DMSO-d$_6$) δ 24.6, 102.7, 114.8, 116.9, 117.0, 130.8, 131.2, 136.8, 144.0, 148.7, 166.4, 168.9; GC-MS (EI, 70 eV): m/z (%) 305 (58) [M$^+$], 307 (57) [M$^+$]; HRMS pos. (ESI): Calc for [M+H]$^+$, C$_{12}$H$_9$BrN$_3$O$_2$: 305.98727 and 307.98532. found: 305.98737 and 307.98544; IR (ATR, cm$^{-1}$): 3079, 2742, 1764, 1707, 1584, 1488, 1440, 1419, 1384, 1287, 1167, 1141, 1101, 801, 778, 733, 628.

Example 1.3

1-Methyl-3,4-bis-(2-methyl-1H-indol-3-yl)-1H-pyrrole-2,5-dione

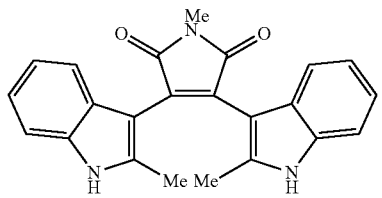 [SMILES: Cc1[nH]c2ccccc2c1C1=C(c2c(C)[nH]c3ccccc23)C(=O)N(C)C1=O]

Red crystals; $^1$H NMR (DMSO-d$_6$) δ 1.97 (s, 3H), 1.98 (s, 3H), 3.05 (s, 3H), 6.75 (br.t, 2H, J=7.41 Hz), 6.95 (ddd, 2H, J~3.83, 5.31, 7.36 Hz), 7.03 (br.d, 2H, J=7.90 Hz), 7.23 (br.d, 2H, J=8.09 Hz), 11.29 (br.s, 2H); $^{13}$C NMR (DMSO-d$_6$) δ 13.0, 23.9, 103.3, 110.7, 119.2, 119.4, 120.8, 126.6, 131.2, 135.5 (2C), 137.3, 170.4, 171.3; GC-MS (EI, 70 eV): m/z (%) 369 (100) [M$^+$]; HRMS (EI): Cacld for C$_{23}$H$_{19}$O$_2$N$_3$: 369.14718. found 369.14705; IR (ATR, cm$^{-1}$): 3383, 3307, 1755, 1692, 1456, 1435, 1377, 1239, 1049, 1022, 1003, 747, 737, 693.

Example 2: Preparation 2—General Procedure for Suzuki Coupling and Specific Compounds In an Ace-pressure tube into a solution of (aza)indolyl-maleimide derivative (1 mmol) and corresponding boronic acid (1.5 mmol) in dimethoxyethane (3 ml) were added K$_2$CO$_3$ (1M in water, 3 ml), Pd(OAc)$_2$ (2 mol %) and ligand (2.5 mol %) under argon atmosphere. The pressure tube was fitted with a Teflon cap and heated at 100° C. (TLC control). The mixture was cooled to room temperature and diluted with ethyl acetate. The organic layer was washed with sat. aq ammonium chloride (2×30 mL) and water. After drying over Na$_2$SO$_4$ and removal of the solvent in vacuum, the coupling product was isolated by column chromatography in heptane/ethyl acetate.

Example 2.4

1-Methyl-3-(2-methyl-1H-indol-3-yl)-4-(4-vinylphenyl)-1H-pyrrole-2,5-dione

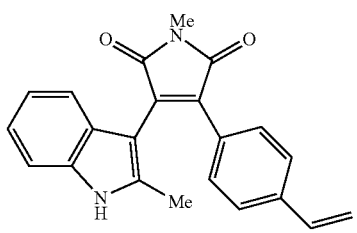 [SMILES: C=Cc1ccc(C2=C(c3c(C)[nH]c4ccccc34)C(=O)N(C)C2=O)cc1]

Red-orange crystals; $^1$H NMR (CDCl$_3$) δ 2.14 (s, 3H), 3.17 (s, 3H), 5.25 (dd, 1H, J=0.66, 10.89 Hz), 5.72 (dd, 1H, J=0.70, 17.61 Hz), 6.63 (dd, 1H, J=10.88, 17.62 Hz), 6.96 (m, 1H), 7.09 (m, 2H), 7.23 (m, 1H), 7.27 (m, 2H), 7.53 (m, 2H), 8.32 (br s, 1H); $^{13}$C NMR (CDCl$_3$) δ 13.7, 24.2, 103.0, 110.5, 115.0, 120.3, 120.5, 122.0, 126.1 (2C), 126.5, 129.5 (2C), 129.6, 132.7, 133.7, 135.7, 136.2, 136.8, 138.1, 171.2, 171.6; GC-MS (EI, 70 eV): m/z (%) 342 (100) [M⁺]; HRMS (EI): Cacld for $C_{22}H_{18}O_2N_2$: 342.13628. found: 342.13618; IR (ATR, cm⁻¹): 3380, 3053, 2920, 1745, 1689, 1456, 1428, 1383, 1235, 990, 903., 847, 814, 741, 656.

Example 2.5

1-Methyl-3-(2-methyl-1H-indol-3-yl)-4-phenyl-1H-pyrrole-2,5-dione

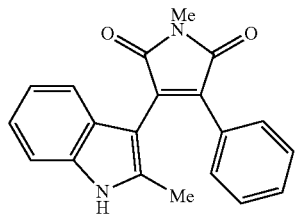 [SMILES: Cc1[nH]c2ccccc2c1C1=C(c2ccccc2)C(=O)N(C)C1=O]

Red crystals; ¹H NMR (CDCl₃) δ 2.14 (s, 3H), 3.20 (s, 3H), 6.97 (ddd, 1H), 7.11 (m, 2H), 7.22 (ddd, 1H), 7.27 (m, 3H), 7.55 (m, 2H), 8.33 (br.s, 1H); ¹³C NMR (CDCl₃) δ 13.6, 24.2, 102.8, 110.5, 120.3, 120.5, 122.0, 126.5, 128.4 (2C), 129.1, 129.3 (2C), 130.2, 133.2, 134.1, 135.7, 136.8, 171.2, 171.5; GC-MS (EI, 70 eV): m/z (%) 316 (100) [M⁺]; HRMS (ED: Cacld for $C_{20}H_{16}O_2N_2$: 316.12063. found: 316.12091; IR (ATR, cm⁻¹): 3426, 3381, 3052, 1759, 1690, 1618, 1435, 1422, 1382, 1234, 1002, 989, 938, 786, 752, 736, 693.

Example 2.6

3-(4-Acetylphenyl)-1-methyl-4-(2-methyl-1H-indol-3-yl)-1H-pyrrole-2,5-dione (PDA-66)

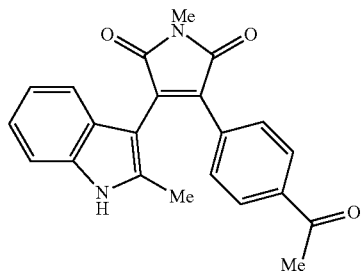 [SMILES: CC(=O)c1ccc(C2=C(c3c(C)[nH]c4ccccc34)C(=O)N(C)C2=O)cc1]

Red crystals; ¹H NMR (CDCl₃) δ 2.18 (s, 3H), 2.57 (s, 3H), 3.21 (s, 3H), 6.94 (ddd, 1H, J~0.99, 7.05, 8.00 Hz), 7.03 (ddd, 1H), 7.11 (ddd, 1H, J~1.15, 7.05, 8.11 Hz), 7.25 (dd, 1H, J~0.41, 8.11 Hz), 7.67 (ddd, 2H, J~1.72, 3.63, 8.61 Hz), 7.84 (ddd, 2H, J~1.85, 3.70, 8.61 Hz), 8.57 (br.s, 1H); ¹³C NMR (CDCl₃) δ 13.8, 24.3, 26.6, 102.5, 110.7, 120.1, 120.6, 122.2, 126.2, 128.2 (2C), 129.5 (2C), 131.9, 134.9, 135.0, 135.8, 136.6, 137.6, 170.8, 171.1, 197.8; GC-MS (EI, 70 eV): m/z (%) 358 (100) [M⁺]; HRMS (EI): Cacld for $C_{22}H_{18}O_3N_2$: 358.13119. found: 358.131088; IR (ATR, cm⁻¹): 3339, 3058, 2923, 1762, 1692, 1678, 1427, 1407, 1383, 1358, 1265, 1234, 990, 846, 817, 742.

Example 2.7

3-(2,6-Dimethylphenyl)-1-methyl-4-(2-methyl-1H-indol-3-yl)-1H-pyrrole-2,5-dione

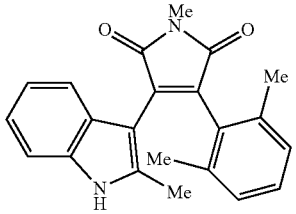 [SMILES: Cc1cccc(C)c1C1=C(c2c(C)[nH]c3ccccc23)C(=O)N(C)C1=O]

Orange crystals; ¹H NMR (CDCl₃) δ 1.97 (d, 3H, J=0.88), 2.08 (s, 6H), 3.22 (s, 3H), 7.00 (ddd, 1H), 7.01 (d, 2H), 7.10 (ddd, 1H), 7.12 (ddd, 1H), 7.19 (ddd, 1H), 7.25 (ddd, 1H), 8.21 (br.s, 1H); ¹³C NMR (CDCl₃) δ 13.2, 20.7 (2C), 24.4, 103.6, 110.3, 119.9, 120.6, 122.1, 126.8, 128.0 (2C), 128.8, 129.5, 135.4, 136.1, 136.9, 137.0 (2C), 137.1, 171.0, 171.2; GC-MS (EI, 70 eV): m/z (%) 344 (100) [M⁺]; HRMS (EI): Cacld for $C_{22}H_{20}O_2N_2$: 344.15193. found: 344.15175; IR (ATR, cm⁻¹): 3342, 2951, 1763, 1689, 1433, 1381, 1229, 987, 739, 665.

Example 2.8

3-(3-Chlorophenyl)-1-methyl-4-(2-methyl-1H-indol-3-yl)-1H-pyrrole-2,5-dione

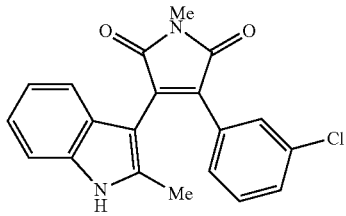 [SMILES: Cc1[nH]c2ccccc2c1C1=C(c2cccc(Cl)c2)C(=O)N(C)C1=O]

Red crystals; ¹H NMR (CDCl₃) δ 2.20 (s, 3H), 3.20 (s, 3H), 6.98 (ddd, 1H, J~1.03, 7.0, 8.03 Hz), 7.05 (br.d, 1H, J~7.52 Hz), 7.13 (ddd, 1H, J~1.23, 7.0, 8.14 Hz), 7.18 (br.t, 1H, J=7.91 Hz), 7.25 (m, 2H), 7.40 (ddd, 1H, J~1.26, 2.72, 7.84 Hz), 7.62 (br.t, 1H, J 1.80 Hz), 8.36 (br.s, 1H); ¹³C NMR (CDCl₃) δ 13.8, 24.3, 102.6, 110.6, 120.3, 120.7, 122.2, 126.2, 127.5, 129.1, 129.2, 129.6, 131.9, 132.1, 134.2, 134.3, 135.85, 137.2, 170.8, 171.1; GC-MS (EI, 70 eV): m/z (%) 350 (100) [M⁺]; HRMS (EI): Cacld for $C_{20}H_{15}O_2N_2Cl$: 350.08166. found: 350.08115; IR (ATR, cm⁻¹): 3350, 3068, 2909, 1764, 1689, 1433, 1383, 1235, 991, 743, 735, 715, 683.

Example 2.9

3-(2,4-Dichlorophenyl)-1-methyl-4-(2-methyl-1H-indol-3-yl)-1H-pyrrole-2,5-dione

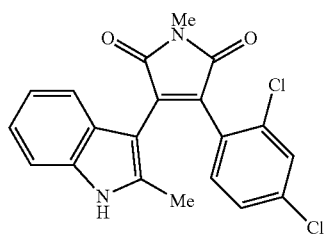 [SMILES: Cc1[nH]c2ccccc2c1C1=C(c2ccc(Cl)cc2Cl)C(=O)N(C)C1=O]

Orange crystals; $^1$H NMR (CDCl$_3$) δ 2.11 (s, 3H), 3.21 (s, 3H), 6.99 (ddd, 1H, J~1.03, 7.0, 8.03 Hz), 7.10 (ddd, 1H, J~0.93, 7.09, 8.23 Hz), 7.18 (m, 2H), 7.19 (d, 2H, J~1.20 Hz), 7.40 (br.t, 1H, J=1.15 Hz), 8.41 (br.s, 1H); $^{13}$C NMR (CDCl$_3$) δ 13.5, 24.4, 103.1, 110.6, 119.7, 120.8, 122.2, 126.7, 127.3, 128.5, 130.1, 132.1, 132.4, 134.7, 135.5, 137.5, 137.6, 170.1, 170.6; GC-MS (EI, 70 eV): m/z (%) 384 (100) [M$^+$]; HRMS (EI): Cacld for C$_{20}$H$_{14}$O$_2$N$_2$Cl$_2$: 384.04268. found: 384.04261; IR (ATR, cm$^{-1}$): 3358, 3064, 2949, 1756, 1687, 1436, 1386, 1228, 992, 857, 810, 778, 741, 673, 666.

Example 2.10

1-Methyl-3-(2-methyl-1H-indol-3-yl)-4-(thiophen-3-yl)-1H-pyrrole-2,5-dione

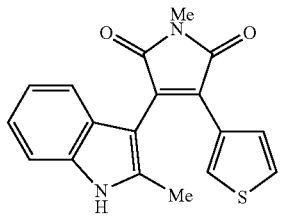 [SMILES: Cc1[nH]c2ccccc2c1C1=C(c2ccsc2)C(=O)N(C)C1=O]

Red crystals; $^1$H NMR (CDCl$_3$) δ 2.27 (s, 3H), 3.18 (s, 3H), 7.01 (ddd, 1H, J~1.07, 7.07, 8.05 Hz), 7.12 (ddd, 1H), 7.137 (dd, 1H, J~3.02, 5.15 Hz), 7.14 (ddd, 1H), 7.19 (dd, 1H, J=1.22, 5.17 Hz), 7.25 (dt, 1H, J=0.91, 8.06 Hz), 8.11 (dd, 1H, J=1.24, 2.95 Hz), 8.42 (br.s, 1H); $^{13}$C NMR (CDCl$_3$) δ 13.5, 24.2, 102.9, 110.6, 120.1, 120.5, 122.0, 125.1, 126.7, 127.5, 129.2, 130.0, 130.2, 130.5, 135.7, 136.7, 171.5, 171.6; GC-MS (EI, 70 eV): m/z (%) 322 (100) [M$^+$]; HRMS (EI): Cacld for C$_{18}$H$_{14}$O$_2$N$_2$S: 322.07705. found: 322.07631; IR (ATR, cm$^{-1}$): 3391, 3102, 1756, 1689, 1624, 1438, 1410, 1382, 1334, 1228, 1071, 1003, 989, 820, 804, 790, 752, 737, 653.

Example 2.11

1-Methyl-3-(2-methyl-1H-indol-3-yl)-4-(pyridin-4-yl)-1H-pyrrole-2,5-dione

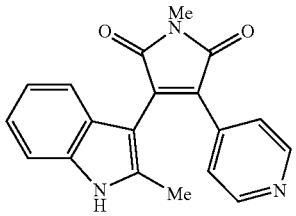 [SMILES: Cc1[nH]c2ccccc2c1C1=C(c2ccncc2)C(=O)N(C)C1=O]

Red crystals; $^1$H NMR (CDCl$_3$) δ 2.28 (s, 3H), 3.21 (s, 3H), 6.97 (m, 2H), 7.14 (ddd, 1H, J~3.58, 4.69, 8.23 Hz), 7.30 (dt, 1H, J~0.7, 8.15 Hz), 7.46 (2dd, 2H, J~1.59, 4.57 Hz), 8.53 (2dd, 2H, J~1.57, 4.62 Hz), 8.71 (br.s, 1H); $^{13}$C NMR (CDCl$_3$) δ 14.1, 24.4, 102.5, 110.8, 120.3, 120.9, 122.5, 123.3 (2C), 125.9, 139.9, 135.9, 136.5, 137.9, 138.1, 149.8 (2C), 170.3, 170.6; GC-MS (EI, 70 eV): m/z (%) 317 (100) [M$^+$]; HRMS (EI): Cacld for C$_{19}$H$_{15}$O$_2$N$_3$: 317.11588. found: 317.11635; IR (ATR, cm$^{-1}$): 3342, 2923, 1765, 1694, 1456, 1428, 1383, 1237, 990, 813, 742, 656.

Example 2.12

1-Methyl-3-(2-methyl-1H-indol-3-yl)-4-(naphthalen-2-yl)-1H-pyrrole-2,5-dione

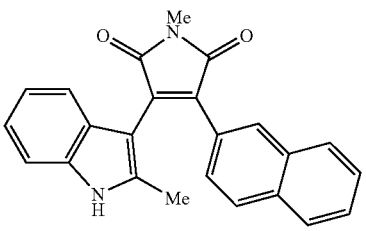 [SMILES: Cc1[nH]c2ccccc2c1C1=C(c2ccc3ccccc3c2)C(=O)N(C)C1=O]

Red crystals; $^1$H NMR (CDCl$_3$) δ 2.09 (s, 3H), 3.24 (s, 3H), 6.95 (ddd, 1H, J~1.04, 7.14, 8.12 Hz), 7.11 (ddd, 1H, J~1.11, 7.13, 8.18 Hz), 7.20 (dd, 1H, J~0.5, 8.12 Hz), 7.25 (dd, 1H, J~<0.5, 8.07 Hz), 7.44 (dd, 1H, J~1.68, 8.58 Hz), 7.48 (m, 2H), 7.59 (br.d, 1H, J~8.71 Hz), 7.74 (m, 1H), 7.83 (m, 1H), 8.33 (br.s, 2H); $^{13}$C NMR (CDCl$_3$) δ 13.7, 24.3, 103.1, 110.5, 120.4, 120.6, 122.1, 125.8, 126.3, 126.8, 127.1, 127.6, 127.7, 127.8, 128.9, 130.0, 133.0, 133.18, 133.22, 133.8, 135.7, 136.9, 171.2, 171.6; GC-MS (EI, 70 eV): m/z (%) 366 (100) [M$^+$]; HRMS (EI): Cacld for C$_{24}$H$_{18}$O$_2$N$_2$: 366.13628. found: 366.13581; IR (ATR, cm$^{-1}$): 3345, 3055, 2946, 1759, 1689, 1425, 1381, 1226, 989, 816, 737, 660.

Example 2.13

3-(2,5-Dimethoxyphenyl)-1-methyl-4-(2-methyl-1H-indol-3-yl)-1H-pyrrole-2,5-dione

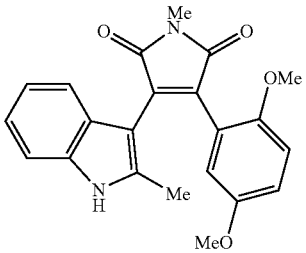 [SMILES: COc1ccc(OC)c(C2=C(c3c(C)[nH]c4ccccc34)C(=O)N(C)C2=O)c1]

Deep orange crystals; $^1$H NMR (CDCl$_3$) δ 2.05 (s, 3H), 3.19 (s, 3H), 3.36 (s, 3H), 3.66 (s, 3H), 6.75 (br.d, 1H, J~8.79 Hz), 6.81 (br.d, 1H, J~2.57 Hz), 6.84 (dd, 1H, J~3.05, 8.80 Hz), 6.94 (ddd, 1H, J~1.13, 7.08, 8.02 Hz), 7.05 (ddd, 1H, J~1.07, 7.15, 8.02 Hz), 7.14 (br.d, 1H, J~8.11 Hz), 7.18 (br.d, 1H, J~7.94 Hz), 8.38 (br.s, 1H); $^{13}$C NMR (CDCl$_3$) δ 13.3, 24.2, 55.78, 55.84, 104.0, 110.2, 112.7, 115.9, 116.2, 119.9, 120.3, 120.6, 121.8, 127.0, 133.3, 135.5, 135.6, 136.6, 151.9 (2C), 153.4 (2C), 171.0, 171.3; GC-MS (EI, 70 eV): m/z (%) 376 (100) [M$^+$]; HRMS (EI): Cacld for C$_{22}$H$_{20}$O$_4$N$_2$: 376.14176. found: 376.14113; IR (ATR, cm$^{-1}$): 3338, 2924, 1750, 1689, 1427, 1383, 1273, 1237, 1212, 1049, 1018, 997, 823, 760, 746, 724, 667.

Example 2.14

1-Methyl-3-(2-methyl-1H-indol-3-yl)-4-(2-(trifluoromethyl)phenyl)-1H-pyrrole-2,5-dione

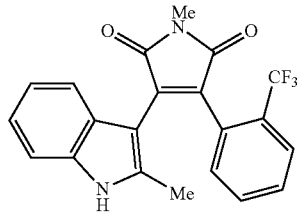 [SMILES: Cc1[nH]c2ccccc2c1C1=C(c2ccccc2C(F)(F)F)C(=O)N(C)C1=O]

Orange crystals; $^1$H NMR (Aceton-d$_6$) δ 2.20 (s, 3H), 3.11 (s, 3H), 6.86 (ddd, 1H, J~1.06, 7.13, 8.07 Hz), 7.00 (ddd, 1H, J~1.16, 7.16, 8.13 Hz), 7.19 (br.d, 1H, J~7.95 Hz), 7.27 (ddd, 1H), 7.37 (m, 1H), 7.55 (m, 2H), 7.76 (m, 1H), 10.55 (br.s, 1H); $^{13}$C NMR (Aceton-d$_6$) δ 13.1, 24.1, 102.3 (d, J=4.55 Hz), 111.2 (d, J=5.13 Hz), 120.0, 120.2, 121.9, 124.9 (q, J=272.93 Hz), 127.7 (q, J=4.42 Hz), 127.9 (d, J=3.68 Hz), 129.6 (q, J=30.37 Hz), 129.9 (d, J=1.79 Hz), 130.0, 132.5 (2C), 135.4, 136.5 (d, J=15.20 Hz), 137.5, 138.4 (d, J=14.52 Hz), 170.87, 170.93; $^{19}$F NMR (CDCl$_3$) δ −57.57 (s); GC-MS (EI, 70 eV): m/z (%) 384 (100) [M$^+$]; HRMS (EI): Cacld for C$_{21}$H$_{15}$O$_2$N$_2$F$_3$: 384.10801. found: 384.10765; IR (ATR, cm$^{-1}$): 3365, 3080, 1768, 1694, 1445, 1385, 1315, 1163, 1118, 1036, 991, 764, 742, 657.

Example 2.15

3-(4-Fluorophenyl)-1-methyl-4-(2-methyl-1H-indol-3-yl)-1H-pyrrole-2,5-dione

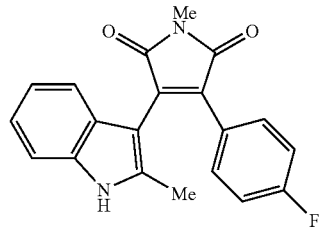 [SMILES: Cc1[nH]c2ccccc2c1C1=C(c2ccc(F)cc2)C(=O)N(C)C1=O]

Orange crystals; $^1$H NMR (CDCl$_3$) δ 2.21 (s, 3H), 3.20 (3, 3H), 6.96 (m, 3H), 7.03 (dd, 1H, J~0.35, 7.75 Hz), 7.12 (ddd, 1H, J~1.24, 6.93, 8.13 Hz), 7.25 (ddd, 1H), 7.59 (ddt, 2H, J~2.90, 5.50, 8.48 Hz), 8.35 (br.s, 1H); $^{13}$C NMR (CDCl$_3$) δ 13.7, 24.2, 102.6, 110.6, 115.4, 115.7, 120.2, 120.6, 122.1, 126.22 (d, J~3.60 Hz), 126.3, 131.4, 131.5, 132.87 (d, J~1.07 Hz), 132.0, 135.8, 136.9, 162.89 (d, J=251.81 Hz), 171.1, 171.5; $^{19}$F NMR (CDCl$_3$) δ −109.8 (s); HRMS (EI): Cacld for C$_{20}$H$_{15}$O$_2$N$_2$F: 334.11121. found: 334.11137; IR (ATR, cm$^{-1}$): 3380, 3042, 1755, 1700, 1600, 1508, 1458, 1427, 1379, 1232, 1159, 996, 841, 813, 750, 731, 657.

Example 2.16

3-(5-Acetyl-2-fluorophenyl)-1-methyl-4-(2-methyl-1H-indol-3-yl)-1H-pyrrole-2,5-dione

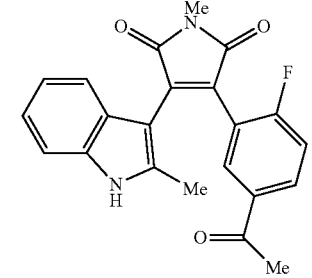 [SMILES: CC(=O)c1ccc(F)c(C2=C(c3c(C)[nH]c4ccccc34)C(=O)N(C)C2=O)c1]

Deep red crystals; $^1$H NMR (Aceton-d$_6$) δ 2.29 (s, 3H), 2.49 (s, 3H), 3.12 (s, 3H), 6.80 (ddd, 1H, J~1.06, 7.15, 8.37 Hz), 7.00 (m, 2H), 7.16 (dd, 1H, J=8.69, 9.51 Hz), 7.30 (dd, 1H, J=0.82, 8.69 Hz), 8.01 (ddd, 1H, J=2.34, 4.90, 8.57 Hz), 8.17 (dd, 1H, J=2.23, 6.79 Hz), 10.65 (br.s, 1H); $^{13}$C NMR (Aceton-d$_6$) δ 13.4, 24.1, 26.3, 103.5, 111.4, 116.6 (d, J=22.4 Hz), 119.9, 120.1 (d, J=16.2 Hz), 120.4, 122.0, 127.4, 128.7 (d, J=2.5 Hz), 131.8 (d, J=9.6 Hz), 133.0 (d, J=4.6 Hz), 134.2 (d, J=3.4 Hz), 136.7, 138.4, 138.9, 163.4 (d, J=259.4 Hz), 170.6, 170.8, 195.9; $^{19}$F NMR (Aceton-d$_6$) δ −102.9 (m); GC-MS (EL 70 eV): m/z (%) 376 (100) [M$^+$]; HRMS pos. (ESI): Calc for [M+H]$^+$, C$_{22}$H$_{18}$FN$_2$O$_3$: 377.1296. found: 377.1302; HRMS pos. (ESI): Calc for [M+Na]$^+$, C$_{22}$H$_{17}$FN$_2$NaO$_3$: 399.11154. found: 399.11152; IR (ATR, cm$^{-1}$): 3351, 1689, 1645, 1602, 1439, 1386, 1353, 1250, 1223, 828, 778, 742, 630, 568, 436, 408.

Example 2.17

N-(4-(1-Methyl-4-(2-methyl-1H-indol-3-yl)-2,5-dioxo-2,5-dihydro-1H-pyrrol-3-yl)phenyl)acetamide

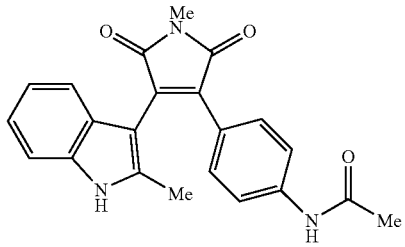 [SMILES: CC(=O)Nc1ccc(C2=C(c3c(C)[nH]c4ccccc34)C(=O)N(C)C2=O)cc1]

Orange crystals; $^1$H NMR (Aceton-d$_6$) δ 2.05 (s, 3H), 2.27 (s, 3H), 3.07 (s, 3H), 6.83 (ddd, 1H, J~0.98, 6.93, 8.06 Hz), 7.00 (d, 1H, J=7.60 Hz), 7.02 (ddd, 1H), 7.32 (ddd, 1H, J~1.00, 2.09, 7.76 Hz), 7.53 (m, 4H), 9.27 (br.s, 1H), 10.59 (br.s, 1H); $^{13}$C NMR (Aceton-d$_6$) δ 13.3, 23.8, 24.0, 103.0, 111.3, 118.8 (2C), 120.1, 120.5, 121.8, 125.9, 127.2, 130.6 (2C), 132.6, 133.8, 136.9, 137.9, 140.7, 168.8, 171.4, 171.9; GC-MS (EI, 70 eV): m/z (%) 373 (100) [M$^+$]; HRMS pos. (ESI): Calc for [M+H]$^+$, C$_{22}$H$_{20}$H$_3$O$_3$: 374.14992. found: 374.15012; HRMS pos. (ESI): Calc for [M+Na]$^+$, C$_{22}$H$_{19}$N$_3$NaO$_3$: 396.13186. found: 396.13226; IR (ATR, cm$^{-1}$): 3379, 1675, 1582, 1505, 1424, 1403, 1386, 1365, 1310, 1237, 1179, 851, 815, 750, 653, 585, 567, 556, 532, 434, 379.

Example 3: Preparation 3—General Procedure for Preparation of Compounds of Formula (II) and (III) and Specific Compounds Step 1. The mixture of compound of formula (I) (1 mmol) wherein X is N—R$^1$, and 100 ml of 10% aq KOH was heated at 140° C. until the mixture become homogenous (10 to 30 min, TLC control). Then the solution was cooled and acidified with 2N aq HCl, until precipitate was formed, which was collected, dried and recrystallized to give nearly quantitatively cyclic anhydride of formula (II).

Step 2. Compound of formula (II) (1 mmol) was heated with ammonium acetate (100 mmol) at 140° C. until the mixture become homogenous (TLC control). The mixture was cooled down, water was added, and the mixture was extracted with ethyl acetate. The combined organics were washed with water, dried over Na$_2$SO$_4$ and concentrated. The crude material was crystallized from ether. The product of formula (III) was isolated by column chromatography in heptane/ethyl acetate.

Example 3.18

3-(2-Methyl-1H-indol-3-yl)-4-phenylfuran-2,5-dione

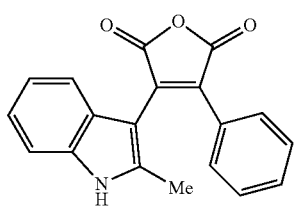 [SMILES: Cc1[nH]c2ccccc2c1C1=C(c2ccccc2)C(=O)OC1=O]

Red crystals; $^1$H NMR (Aceton-d$_6$) δ 2.31 (s, 3H), 6.86 (ddd, 1H, J~1.03, 7.06, 8.08 Hz), 7.02 (ddd, 1H), 7.07 (ddd, 1H, J~1.14, 7.17, 8.21 Hz), 7.36 (m, 4H), 7.60 (m, 2H), 10.83 (br.s, 1H); $^{13}$C NMR (Aceton-d$_6$) δ 13.4, 102.2, 111.6, 120.6 (2C), 122.4, 126.7, 128.9 (2C), 129.9 (2C), 130.2, 130.4, 134.9, 136.1, 136.9, 139.7, 166.1, 166.3; GC-MS (EI, 70 eV): m/z (%) 303 (52) [M$^+$]; HRMS (EI): Calc for C$_{19}$H$_{13}$O$_3$N: 303.08899. found: 303.08861; IR (ATR, cm$^{-1}$): 3350, 2921, 2852, 1825, 1749, 1618, 1456, 1423, 1252, 902, 741, 726, 693, 671, 635, 622, 564, 531.

Example 3.19

3-(2-Methyl-1H-indol-3-yl)-4-phenyl-1H-pyrrole-2,5-dione

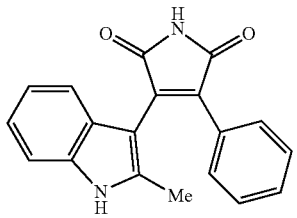 [SMILES: Cc1[nH]c2ccccc2c1C1=C(c2ccccc2)C(=O)NC1=O]

Red crystals; $^1$H NMR (Aceton-d$_6$) δ 2.24 (s, 3H), 6.83 (ddd, 1H, J~1.01, 7.08, 8.01 Hz), 7.02 (ddd, 1H), 7.03 (d, 1H, J=7.58 Hz), 7.27 (m, 3H), 7.31 (ddd, 1H), 7.54 (m, 2H), 9.83 (br.s, 1H), 10.56 (br.s, 1H); $^{13}$C NMR (Aceton-d$_6$) δ 13.2, 102.8, 111.2, 120.1, 120.5, 121.8, 127.3, 128.6 (2C), 129.3, 130.0 (2C), 131.3, 134.8, 134.9, 136.8, 138.0, 171.7, 172.2; GC-MS (EI, 70 eV): m/z (%) 302 (100) [M$^+$]; HRMS (EI): Calc for C$_{19}$H$_{14}$O$_2$N$_2$: 302.10498. found: 302.105426; IR (ATR, cm$^{-1}$): 3379, 3205, 3065, 2917, 2764, 1764, 1704, 1598, 1451, 1423, 1335, 1289, 1278, 1227, 1013, 993, 770, 754, 729, 719, 690.

Example 3.20

3-(2-Methyl-1H-indol-3-yl)-4-(naphthalen-2-yl)furan-2,5-dione

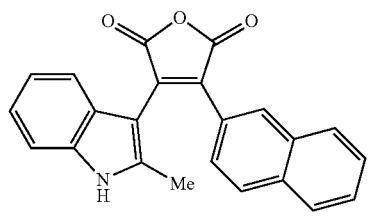 [SMILES: Cc1[nH]c2ccccc2c1C1=C(c2ccc3ccccc3c2)C(=O)OC1=O]

Orange crystals; $^1$H NMR (CDCl$_3$) δ 2.30 (s, 3H), 6.81 (ddd, 1H), 7.05 (ddd, 2H), 7.37 (ddd, 1H), 7.53 (m, 3H), 7.75 (d, 1H, J~8.62 Hz), 7.87 (m, 2H), 8.36 (s, 1H), 10.86 (s, 1H); $^{13}$C NMR (CDCl$_3$) δ 13.3, 102.5, 111.6, 120.6, 120.7, 122.4, 126.0, 126.9, 127.2, 127.7, 128.16, 128.24, 128.4, 129.3, 130.7, 133.5, 134.1, 134.7, 136.1, 136.9, 139.9, 166.1, 166.4; MS (EI): m/z (%) 353 (650) [M$^+$]; HRMS pos. (ESI): Calc for [M+H]$^+$, C$_{23}$H$_{16}$NO$_3$: 354.11247. found: 354.11221; HRMS pos. (ESI): Calc for [M+Na]$^+$, C$_{23}$H$_{15}$NNaO$_3$: 376.09441. found: 376.09419; IR (ATR, cm$^{-1}$): 3366, 2926, 1757, 1460, 1428, 1259, 1242, 1222, 1158, 910, 784, 766, 737, 590, 554, 475.

Example 3.21

3-(2-Methyl-1H-indol-3-yl)-4-(naphthalen-2-yl)-1H-pyrrole-2,5-dione

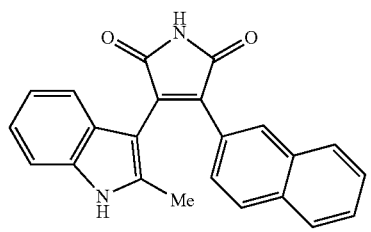 [SMILES: Cc1[nH]c2ccccc2c1C1=C(c2ccc3ccccc3c2)C(=O)NC1=O]

Orange crystals; $^1$H NMR (Aceton-d$_6$) δ 2.24 (s, 3H), 6.77 (ddd, 1H, J~1.04, 7.12, 8.07 Hz), 7.00 (ddd, 1H, J~1.15, 7.10, 8.07 Hz), 7.08 (d, 1H, J=8.0 Hz), 7.33 (ddd, 1H, J~0.85, 8.08), 7.48 (m, 3H), 7.66 (d, 1H, J=8.8 Hz), 7.80 (m, 1H), 7.84 (m, 1H), 8.30 (d, 1H, J=0.72 Hz), 9.90 (br.s, 1H), 10.60 (br.s, 1H); $^{13}$C NMR (Aceton-d$_6$) δ 13.3, 103.1, 111.3, 120.2, 120.5, 121.9, 126.6, 126.9, 127.5 (2C), 128.0, 128.1, 128.9, 129.1, 130.4, 133.6, 133.7, 134.5, 135.0, 136.8, 138.3, 171.7, 172.3; MS (EI): m/z (%) 352 (100) [M$^+$]; HRMS (EI): Calc for C$_{23}$H$_{16}$O$_2$N$_2$: 352.12063. found: 352.120553; IR (ATR, cm$^{-1}$): 3379, 3209, 3062, 2959, 2925, 2738, 1762, 1702, 1621, 1457, 1426, 1329, 1290, 1222, 1034, 993, 858, 826, 786, 754, 742, 715, 670, 662.

Example 3.22

3-(4-Acetylphenyl)-4-(2-methyl-1H-indol-3-yl)furan-2,5-dione

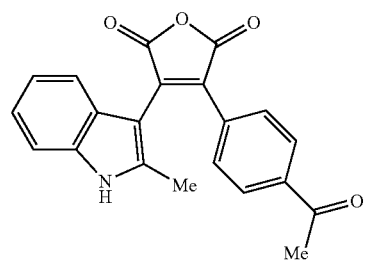 [SMILES: CC(=O)c1ccc(C2=C(c3c(C)[nH]c4ccccc34)C(=O)OC2=O)cc1]

Red-orange crystals; $^1$H NMR (CDCl$_3$) δ 2.33 (s, 3H), 2.56 (s, 3H), 6.86 (ddd, 1H, J~1.0, 7.04, 8.08 Hz), 6.99 (br. d, 1H, J~8.0 Hz), 7.07 (ddd, 1H, J~1.22, 7.02, 8.12 Hz), 7.34 (ddd, 1H, J~0.80, 0.84, 8.10), 7.72 (ddd, 2H), 7.94 (ddd, 2H), 10.98 (br.s, 1H); $^{13}$C NMR (CDCl$_3$) δ 13.5, 26.4, 102.3, 111.7, 120.6, 120.8, 122.5, 126.5, 128.6 (2C), 130.1 (2C), 133.3, 134.5, 136.9, 137.5, 138.0, 140.4, 165.9, 166.0, 197.2; GC-MS (EI, 70 eV): m/z (%) 345 (87) [M$^+$]; HRMS (EI): Calc for C$_{21}$H$_{15}$O$_4$N: 345.09956. found: 345.09942; IR (ATR, cm$^{-1}$): 3233, 2921, 2852, 1759, 1671, 1460, 1252, 1186, 1112, 924, 831, 747, 731, 628, 591, 578, 516, 456, 434, 416.

Example 3.23

3-(4-Acetylphenyl)-4-(2-methyl-1H-indol-3-yl)-1H-pyrrole-2,5-dione

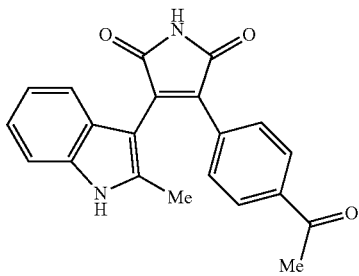 [SMILES: CC(=O)c1ccc(C2=C(c3c(C)[nH]c4ccccc34)C(=O)NC2=O)cc1]

Orange crystals; $^1$H NMR (Aceton-d$_6$) δ 2.28 (s, 3H), 2.53 (s, 3H), 6.82 (ddd, 1H, J~1.03, 7.07, 8.03 Hz), 6.99 (br. d, 1H, J~7.40 Hz), 7.02 (ddd, 1H, J~1.12, 7.07, 8.11 Hz), 7.33 (ddd, 1H, J~0.81, 0.95, 8.08), 7.66 (ddd, 2H), 7.87 (ddd, 2H), 9.93 (br.s, 1H), 10.67 (br.s, 1H); $^{13}$C NMR (Aceton-d$_6$) δ 13.4, 26.4, 102.8, 111.4, 120.3, 120.5, 122.0, 127.1, 128.4 (2C), 130.2 (2C), 133.3, 135.9, 136.3, 136.9, 137.2, 138.7, 171.4, 171.8, 197.2; GC-MS (EI, 70 eV): m/z (%) 344 (100) [M$^+$]; HRMS (EI): Calc for C$_{21}$H$_{16}$O$_3$N$_2$: 344.11554. found: 344.11495; IR (ATR, cm$^{-1}$): 3343, 3296, 3057, 1757, 1699, 1676, 1428, 1343, 1262, 1230, 740, 666, 638, 595, 460, 409.

Example 3.24

3-(4-Acetylphenyl)-4-(1,2-dimethyl-1H-indol-3-yl)-1-methyl-1H-pyrrole-2,5-dione

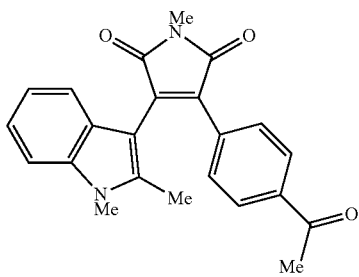 [SMILES: CC(=O)c1ccc(C2=C(c3c(C)n(C)c4ccccc34)C(=O)N(C)C2=O)cc1]

Dark red crystals; $^1$H NMR (DMSO-d$_6$) δ 2.18 (s, 3H), 2.52 (s, 3H), 3.03 (s, 3H), 3.71 (s, 3H), 6.84 (ddd, 1H), 6.93 (br.d, 1H, J~7.54 Hz), 7.08 (ddd, 1H, J~1.06, 7.08, 8.14 Hz), 7.45 (br.d, 1H, J~8.25 Hz), 7.56 (br.d, 2H, J~8.50 Hz), 7.86 (br.d, 2H, J~8.50 Hz); $^{13}$C NMR (DMSO-d$_6$) δ 12.3, 24.2, 26.8, 29.9, 101.3, 109.9, 119.7, 119.9, 121.3, 125.1, 128.1 (2C), 129.3 (2C), 131.6, 134.6, 135.1, 136.2, 137.1, 139.6, 170.4, 170.7, 197.5; GC-MS (EI, 70 eV): m/z (%) 372 (100) [M$^+$]; HRMS pos. (ESI): Calc for [M+H]$^+$, C$_{23}$H$_{21}$N$_2$O$_3$: 373.15467. found: 373.15473; IR (ATR, cm$^{-1}$): 3433, 2915, 1759, 1680, 1599, 1433, 1404, 1382, 1359, 1265, 1240, 957, 849, 829, 749, 738, 726, 595, 546, 439.

Example 3.25

3-(4-Acetylphenyl)-1-methyl-4-(1H-pyrrolo[2,3-b]yridine-3-yl)-1H-pyrrole-2,5-dione

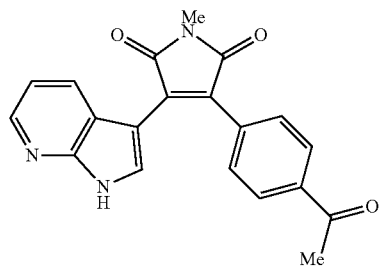 [SMILES: CC(=O)c1ccc(C2=C(c3c[nH]c4ncccc34)C(=O)N(C)C2=O)cc1]

Yellow crystals; $^1$H NMR (DMSO-d$_6$) δ 2.57 (s, 3H), 3.04 (s, 3H), 6.66 (dd, 1H, J~0.89, 8.00 Hz), 6.80 (dd, 1H, J~4.74, 7.96 Hz), 7.55 (br.d, 2H, J~8.27 Hz), 7.93 (br.d, 2H, J~8.20 Hz), 8.11 (s, 1H), 8.18 (br.d, 2H, J~3.70 Hz), 12.55 (br.s, 1.H); $^{13}$C NMR (DMSO-d$_6$) δ 24.1, 26.8, 102.8, 116.28, 116.34, 128.0 (2C), 128.4, 129.1, 129.9 (2C), 131.8, 132.5, 134.8, 136.5, 143.7, 149.0, 170.6, 170.8, 197.5; GC-MS (EI, 70 eV): m/z (%) 345 (100) [M$^+$]; HRMS pos. (ESI): Calc for [M+H]$^+$, C$_{20}$H$_{16}$N$_3$O$_3$: 346.11862. found: 346.11828; IR (ATR, cm$^{-1}$): 3025, 2873, 2817, 1756, 1695, 1677, 1440, 1421, 1385, 1289, 1269, 1229, 1090, 814, 776, 750, 645, 596, 514.

Example 4: Biological Methods

Human neural progenitor cells ReNcell VM (Millipore, Schwalbach, Germany) were cultured on laminin-coated culture-vessels. Culture medium consisted of DMEM/F12 supplemented with B27 media supplement, GlutaMax™, gentamycin and heparin sodium salt and growth factors EGF (epidermal growth factor) and bFGF (basic fibroblast growth factor). The human neuroblastoma cell line SH-SY5Y was obtained from the German Resource Centre for Biological Material DSMZ (Braunschweig, Germany). Cells were cultivated in DMEM, supplemented with 10% FBS, 1% Penicillin-Streptomycin, 4 mM L-Glutamine. The human T cell leukemia cell line Jurkat was obtained from the German Resource Centre for Biological Material DSMZ (Braunschweig, Germany). Cells were cultivated in RPMI 1640 medium, supplemented with 10% FBS, 1% Penicillin-Streptomycin. The murine melanoma cell line B16F10 was obtained from the American Type Culture Collection (ATCC, Manassas, USA), Cells were cultivated in DMEM/GM medium supplemented with 10% FBS, 1% Penicillin-Streptomycin. The mammary gland/breast carcinoma cell line MCF-7 was obtained from American Type Culture Collection (ATCC, Manassas, USA) and cultivated according to standard proceedings in Eagle's Minimum Essential Medium (EMEM). The colon carcinoma cell line SW480 was obtained from American Type Culture Collection (ATCC, Manassas, USA) and cultivated according to standard proceedings in Leibovitz's L15 Medium. The lung carcinoma cell line A549 was obtained from American Type Culture Collection (ATCC, Manassas, USA) and cultivated according to standard proceedings in F-12K Medium (Kaighn's Modification of Ham's F-12 Medium). The liver carcinoma cell line Hep G2 was obtained from American Type Culture Collection (ATCC, Manassas, USA) and cultivated according to standard proceedings in Eagle's Minimum Essential Medium (EMEM).

Cell Proliferation and Vitality Assay

Cell proliferation and vitality were measured with a CASY Model TT (Roche, Mannheim, Germany) by electrical current exclusion method. Cells were seeded in defined numbers into 48-well-plates and proliferated for 24 h. Subsequently fresh medium was applied containing compounds or DMSO, in the following referred as control.

VEC-DIC Microscopy of Tubulin Polymerization

In order to evaluate interference with tubulin polymerisation bovine neuronal tubulin was used, diluted in BRB80 buffer (80 mM PIPES, pH 6.8; MgCl2 1 mM; EGTA 1 mM) at a concentration of 2 mg/ml. After addition of 0.5 mM GTP and 10% DMSO, initiating tubulin polymerisation, the solution samples were incubated at 37° C. in the presence of compound of example 6 (PDA-66). After 1 h the samples were analysed by using video enhanced contrast differential interference contrast (VEC-DIC) microscopy.

Tubulin Polymerisation Turbidity Assay

Purified bovine brain tubulin was used to measure tubulin-polymerisation by determining turbidity in tubulin samples incubated with compound of example 6 (PDA-66), paclitaxel or nocodazole (all 1 μM) and 0.6% DMSO in water as negative control. Optical density (OD) was measured after initiation of tubulin assembly at a wavelength of 340 nm continuously for 60 min in 1 min intervals at a temperature of 37° C. in a plate reader (Tecan, Mainz, Germany).

AnnexinV/PI Apoptosis Detection

To determine the amount of apoptotic and necrotic cells a FITC AnnexinV Apoptosis Detection Kit I was used. For FACS analysis, cells were trypsinised and centrifuged at 100×g at RT for 5 min and washed with PBS without Ca$^{2+}$ and Mg$^{2+}$. Annexin V and propidium iodide (PI) were added accordingly to the manufacture's instructions. After 15 min incubation at room temperature on a shaker in the dark, the measurement was done by using FACSCalibur (Becton Dickinson, San Jose, USA) in combination with Cell Quest Pro software.

Chemicals mentioned in "Biological Methods" were obtained from:
Sigma-Aldrich (Hamburg, Germany): DMSO, PIPES, MgCl2, EGTA, GTP, paclitaxel, nocodazole, PDL, PFA, TritonX-100, primary antibody for α-tubulin. Invitrogen (Karlsruhe, Germany): GlutaMax™, gentamycin, heparin sodium salt DMEM/F12, B27 media supplement. Roche (Mannheim, Germany): EGF (epidermal growth factor), bFGF (basic fibroblast growth factor. GIBCO (Berlin, Germany): DMEM, L-Glutamine. PAA (Cölbe, Germany): FBS. Biochrome (Berlin, Germany): Penicillin-Streptomycin. Cytoskeleton (Denver, USA): bovine neuronal tubulin BK006P. AMS Biotechnology (Frankfurt, Germany): laminin. Molecular Probes (Darmstadt, Germany): Alexa Fluor 568. BD Bioscience (Heidelberg, Germany): FITC AnnexinV Apoptosis Detection Kit I.

Example 5: Biological Data 5.1 Cytotoxic effects were evaluated using human fetal cells immortalized by transfection with the oncogen v-myc (Donato et al., Differential development of neuronal physiological responsiveness in two human neural stem cell lines. BMC Neurosci.; 8, 2007), also referred to herein as human neuronal progenitor cells, hNPCs, or ReNcell VM, providing a sensitive screening system and cancer cells, namely SH5Y5, Jurkat and B16F10 cells. Cytotoxic effects were measured by comparison of cells numbers of DMSO treated cells (control) and cell numbers of cells treated with compound of above mentioned example 2.6 (PDA66). Cell proliferation and vitality was measured with a CASY Model TT (Roche, Mannheim, Germany) by electrical current exclusion method. Cells were seeded in defined numbers into 48-well-plates and proliferated for 24 h: Subsequently fresh medium was applied containing compound of example 6 (3 μM) (PDA-66) or DMSO, in the following referred as control. Cell number and cell vitality was measured after 72 h.

The results are shown in FIG. 1. Cell numbers were measured by the current exclusion method where the number of cells and the vitality cells was assessed simultaneously. Untreated cells showed an exponential growth over time (FIG. 1A, black dots) where the vitality was stable over time (B black dots). Cells treated with compound of example 2.6 (PDA-66) did not proliferate (A black squares) and showed a decreasing vitality (FIG. 1 B, black squares) demonstrating the antiproliferativ effect of compound of example 2.6 (PDA-66).

Compound of example 6 (PDA-66) demonstrated strong significantly antiproliferative effect on immortalized cells (FIG. 1). In comparison to control, cells treated with compound of example 2.6 (PDA-66) showed no proliferation (FIG. 1, left panel). After 72 h of treatment cell number was even lower than the number of seeded cells. In addition the number of vital cells, measured in parallel by the current exclusion method was significantly lower in cells treated with compound of example 2.6 (PDA-66) (FIG. 1, right panel).

Figure 6:
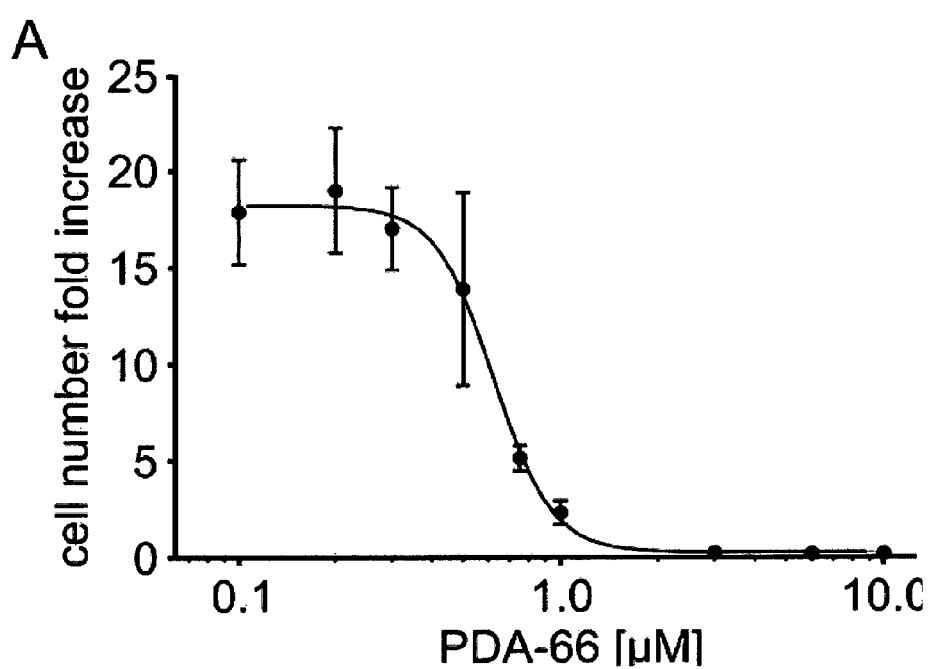
FIG. 6 is a diagram indicating the number of human neuronal progenitor cells (hNPCs), expressed as fold increase, as a function of PDA-66 concentration.

The immortalized cells were also tested to determine whether there is a dose-dependent effect of the compound of example 2.6 (PDA-66) on the proliferation of said immortalized cells. The results are shown in FIG. 6. As may be taken from FIG. 6 there is a dose-dependent effect of the compound of example 2.6 (PDA-66) on the proliferation of said immortalized cells.

Figure 2:
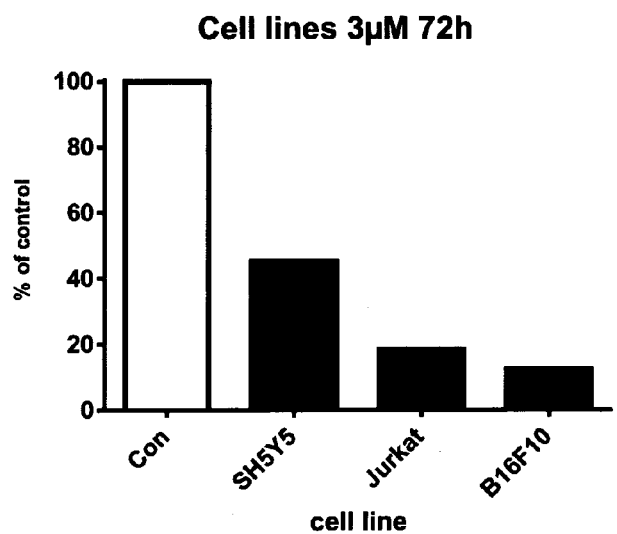
FIG. 2 is a bar diagram showing the inhibitory effect of 3 µM PDA-66 on growth of SH5Y5 cells, Jurkat cells and B16F10 cells.

5.2 Furthermore cancer cells were treated with compound of example 2.6 (PDA-66) with a concentration of 3 μM for 72 h and cell number was evaluated using the current exclusion method as described above. Cell numbers of human neuroblastoma cells (SH5Y5), human T cell leukemia (Jurkat) and murine melanoma cells (B16F10) were reduced or attenuated significantly by the treatment with compound of example 2.6 (PDA-66) demonstrating the anti proliferative effect (FIG. 2).

Figure 7:
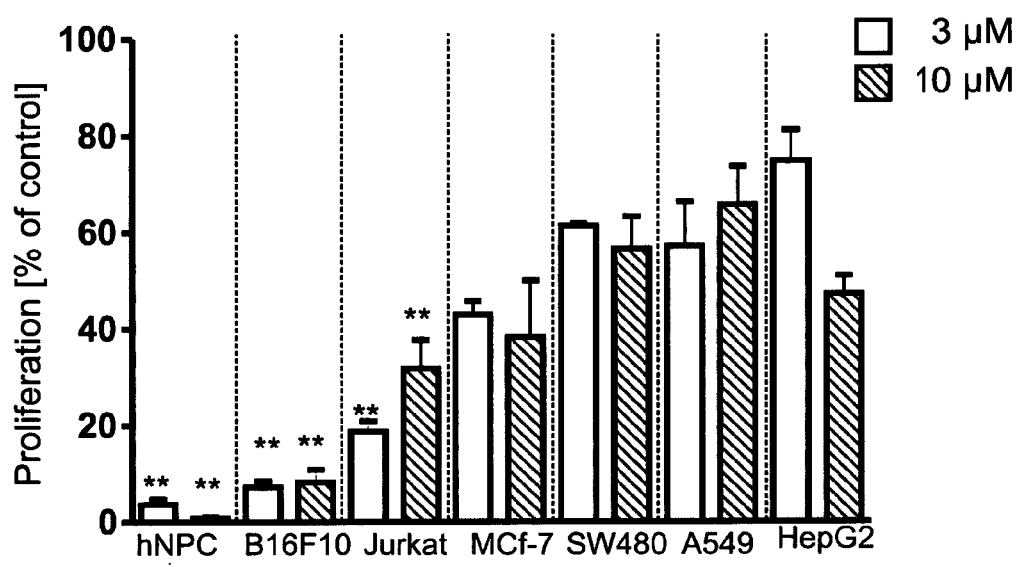
FIG. 7 is a bar diagram showing the inhibitory effect of 3 µM PDA-66 (first bar of each experiment) and 10 µM PDA-66 on growth of hNPC cells, B16F10 cells, Jurkat cells, MCF-7 cells, SW480 cells, A 549 cells and HepG2 cells.

In a further experiment further cancer cells were treated with compound of example 2.6 (PDA-66) with a concentration of 3 μM or 10 μM for 72 h and cell number was evaluated using the current exclusion method as described above. Cell numbers of immortalized human neuronal progenitor cells (hNPCs; proliferation relative to control at 3 μM:3.6±1.2%; and at 10 μM: 0.9±0.2%), human T cell leukemia (Jurkat; proliferation relative to control at 3 μM:18.2±2.2%; and at 10 μM:31.9±5.9%), murine melanoma cells (B16F10; proliferation relative to control at 3 μM:7.2±1.3%; and at 10 8.3±2.6%), mamma carcinoma cells (MCF-1; proliferation relative to control at 3 μM:43.0±2.8%; and at 10 μM: 38.3±11.8%), colon carcinoma cells (SW480; proliferation relative to control at 3 μM: 61.3±0.6%; and at 10 μM: 56.6±6.6%), lung carcinoma cells (A 549; proliferation relative to control at 3 μM:57.1±9.2%; and at 10 μM:65.7±8.0%) and liver carcinoma cells (HepG2; proliferation relative to control at 3 μM:74.8±6.3%; and at 10 μM: 47.2±3.8%) were evidently reduced or attenuated significantly after 72 h by the treatment with compound of example 2.6 (PDA-66) demonstrating the anti-proliferative effect (FIG. 7).

The IC50 value for the compound of example 2.6 (PDA-66), expressed as nM, was 532.3 in case of hNPCs, 1073.0 in case of B16F10 cells, and 8981.0 in case of A549 cells.

Figure 3:
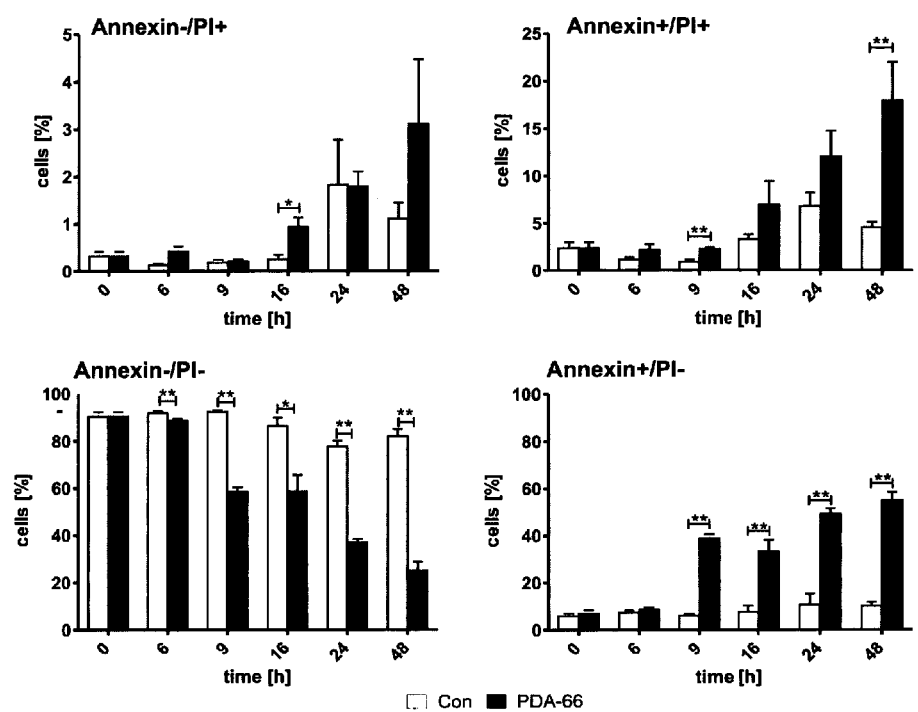
FIG. 3 shows a panel of four bar diagrams indicating percentage of apoptotic cells over time upon exposure to compound PDA-66 with cells being annexin–/PI+, annexin+/PI+, annexin–/PI– or annexin+/PI–.

5.3 It was revealed that the cytoxic effect was most likely based on induction of apoptosis as an increase of apoptotic cells demonstrated by the increase of AnnexinV$^+$/PI$^-$ and AnnexinV$^+$/PI$^+$ cells upon treatment of the cells with compound of example 2.6 (PDA-66) was observed, as may be taken from FIG. 3, right lower and upper panel.

5.4 Induction of apoptosis in proliferative cells, as cancer cells or immortalized cells, can be based on an arrest of the cells within the cell cycle. Such a mitotic arrest can trigger apoptotic cascades as the cells, e.g., do not pass mitotic check points.

Figure 4:
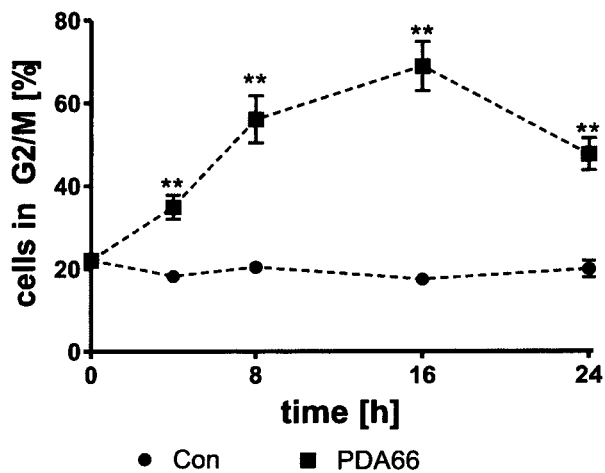
FIG. 4 shows the percentage of cells in G2/M upon exposure to compound PDA66.

A mitotic arrest of cells in the G2/M phase of cell cycle was demonstrated for human immortalized cells treated with compound of example 2.6 (PDA-66) (FIG. 4) where the highest amount of cells was found after 16 h (68.9±10.3% vs. control 17.4±2.3%). As a measure the increase in cells with double DNA content was used, where at all points in time the amount of treated cells was higher in comparison to untreated cells.

5.5 Mitotic arrest is described to be based on a disturbance of the microtubule assembly, where the depolymerising potential of indoles is known (Brancaleand Silvestri, Indole, a core nucleus for potent inhibitors of tubulin polymerization. Med. Res. Rev., 27, 2007).

Figure 5:
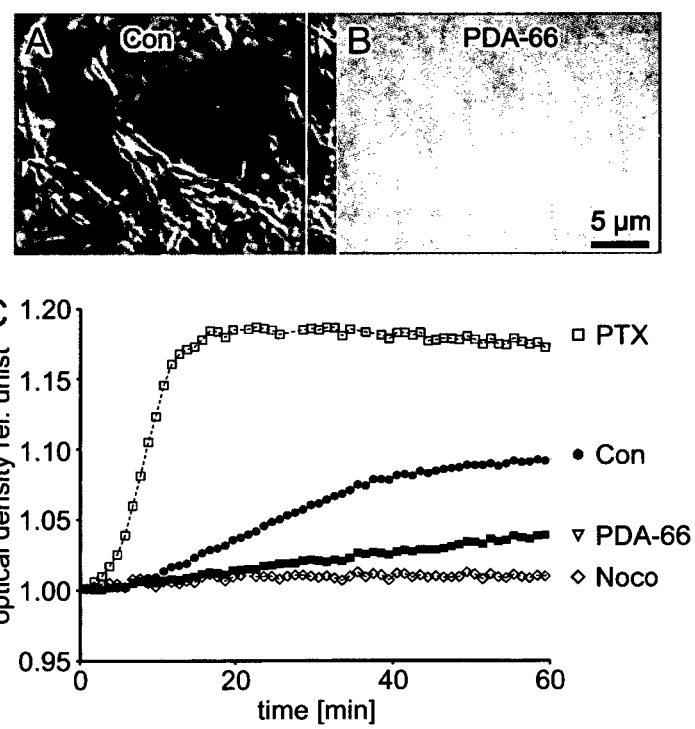
FIG. 5A is a microphotograph view of cells not exposed to PDA-66.
FIG. 5B is a microphotograph view of cells exposed to PDA-66.
FIG. 5C is a diagram showing optical density over time in a polymerization assay using tubulin upon exposure to various compounds, including PDA-66.

The ability of compound of example 2.6 (PDA-66) to hinder polymerization of tubulin was demonstrated by assays employing purified tubulin (FIG. 5A, B). Tubulin was treated with the compound of example 2.6 and by using video enhanced differential interference contrast (VEC-DIC) microscopy the influence of compound of example 6 (PDA-66) on microtubule polymerization was proved. Untreated tubulin was able to build up MTs (FIG. 5A), i.e. to polymerize, whereas in comparison compound of example 2.6 (PDA-66) hindered the MT-polymerization and no bundles or bundle-like structures were observed (FIG. 5B).

The effect of compound of example 2.6 (PDA-66) was also demonstrated in a polymerization assay with purified tubulin using a photometric density measurement (FIG. 5C). Untreated tubulin was used as a control, where the measurement over the time resulted in a sigmoid shaped curve. The obtained curve for paclitaxel possessed a comparable shape but with a steeper slope, typical for microtubule stabilizing agents. In contrast the application of nocodazol, a microtubule destabilizing agent, resulted in a nearly linear curve, indicating that the polymerization of tubulin was hindered. A comparable result was obtained with tubulin treated with compound of example 2.6 (PDA-66), suggesting a destabilizing action of compound of example 2.6 (PDA-66) on tubulin. Consequently, the maximal OD after 60 min was highest for paclitaxel treated tubulin (1.18 rd. units) and lowest for nocodazole (1.01 rel. units) and PDA-66 (1.04 rel. units). Accordingly, compound of example 2.6 (PDA-66) destabilized tubulin in a way comparable to nocodazole, a known microtubule destabilizing agent.

The features of the present invention disclosed in the specification, the claims, the sequence listing and/or the drawings may both separately and in any combination thereof be material for realizing the invention in various forms thereof.

The invention claimed is:

1. A method of treatment of cancer, wherein the method comprises administering to a subject in need thereof, a therapeutically effective amount of a compound of the following structure, or pharmaceutically acceptable salts thereof:

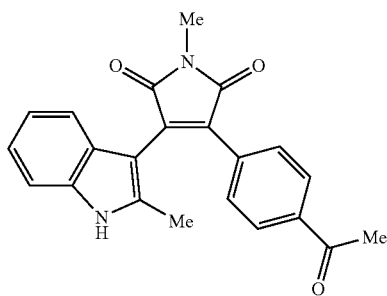 [SMILES: CC(=O)c1ccc(C2=C(c3c(C)[nH]c4ccccc34)C(=O)N(C)C2=O)cc1]

wherein the cancer is selected from the group consisting of breast cancer, liver cancer, mamma carcinoma, lung cancer, colon cancer, gastrointestinal cancer, melanoma, glioma, myeloma, colorectal cancer, neuroblastoma, brain cancer, gastric cancer, and any metastases of any thereof.

2. The method of claim 1, wherein the compound is 3-(4-Acetylphenyl)-1-methyl-4-(2-methyl-1H-indol-3-yl)-1H-pyrrole-2,5-dione.

3. The method of claim 1, further comprising administering a second therapeutic agent, wherein the second therapeutic agent is a chemotherapeutic agent.

4. The method of claim 3, wherein the chemotherapeutic agent is selected from the group consisting of cytarabine, etoposide, mitoxantron, cyclophosphamide, retinoic acid, daunorubicin, doxorubicin, idarubicin, azacytidine, decitabine, a tyrosine-kinase inhibitor, a antineoplastic antibody, vinca_alkaloids and steroids.

5. The method of claim 4, wherein the chemotherapeutic agent is a tyrosine kinase inhibitor, wherein the tyrosine kinase inhibitor is selected from the group consisting of sorafenib, dasatinib, nilotinib, nelarabine and fludarabine, or wherein the chemotherapeutic agent is alemtuzumab.

6. The method of claim 1, wherein the compound has an antiproliferative effect on cells of the cancer.

* * * * *